US011013933B2

(12) United States Patent
Cheng et al.

(10) Patent No.: US 11,013,933 B2
(45) Date of Patent: May 25, 2021

(54) **METHOD AND DEVICE FOR ANNIHILATION OF METHICILLIN-RESISTANT *STAPHYLOCOCCUS AUREUS***

(71) Applicant: Purdue Research Foundation, West Lafayette, IN (US)

(72) Inventors: Ji-Xin Cheng, Newton, MA (US); Mohamed Seleem, West Lafayette, IN (US); Pu-Ting Dong, Boston, MA (US); Jie Hui, Boston, MA (US)

(73) Assignee: Purdue Research Foundation, West Lafayette, IN (US)

( * ) Notice: Subject to any disclaimer, the term of this patent is extended or adjusted under 35 U.S.C. 154(b) by 344 days.

(21) Appl. No.: 16/139,127

(22) Filed: Sep. 24, 2018

(65) Prior Publication Data

US 2019/0126063 A1     May 2, 2019

Related U.S. Application Data

(60) Provisional application No. 62/561,765, filed on Sep. 22, 2017.

(51) Int. Cl.
*A61N 5/06*     (2006.01)
*C12N 13/00*    (2006.01)
(Continued)

(52) U.S. Cl.
CPC .......... *A61N 5/0624* (2013.01); *A61K 31/431* (2013.01); *A61K 31/496* (2013.01);
(Continued)

(58) Field of Classification Search
CPC .. A61N 5/0624; A61N 5/0616; A61N 5/0603; C12N 13/00
See application file for complete search history.

(56) References Cited

U.S. PATENT DOCUMENTS

2007/0255356 A1* 11/2007 Rose ................... A61N 5/0624
607/88
2017/0197993 A1* 7/2017 Cosa .................. A61K 41/0057

OTHER PUBLICATIONS

Photomedicine and Laser Surgery vol. 27, No. 2, 2009, pp. 221-226.
(Continued)

*Primary Examiner* — Kevin Joyner
(74) *Attorney, Agent, or Firm* — Purdue Research Foundation; Liang Zeng Yan

(57) ABSTRACT

Methicillin-resistant *Staphylococcus aureus* (MRSA) possesses array of strategies to evade antibiotics through mutational inactivation, hiding inside host immune cells or concealing inside the biofilm in a sessile form. We report a drug-free approach to eradicate MRSA through blue-light bleaching of staphyloxanthin (STX), an anti-oxidative carotenoid residing inside the cell membrane of *S. aureus*. The photobleaching process, uncovered through a transient absorption imaging study and quantitated by mass spectrometry, decomposes STX and sensitizes MRSA to reactive oxygen species attack. Consequently, photobleaching using low-level blue light exhibits high-level synergy when combined with low-concentration of hydrogen peroxide. Antimicrobial effectiveness of this synergistic therapy is validated in MRSA culture, MRSA-infected macrophage cells, biofilm, and a mouse wound infection model. Collectively, these findings highlight broad applications of STX photobleaching for MRSA-infected diseases.

11 Claims, 41 Drawing Sheets

(51) Int. Cl.
    *A61K 31/546*     (2006.01)
    *A61K 31/7036*     (2006.01)
    *A61K 31/496*     (2006.01)
    *A61K 38/12*     (2006.01)
    *A61K 31/431*     (2006.01)
    *A61N 5/067*     (2006.01)

(52) U.S. Cl.
    CPC ........ *A61K 31/546* (2013.01); *A61K 31/7036* (2013.01); *A61K 38/12* (2013.01); *A61N 5/0603* (2013.01); *C12N 13/00* (2013.01); *A61N 5/0616* (2013.01); *A61N 2005/0605* (2013.01); *A61N 2005/0607* (2013.01); *A61N 2005/067* (2013.01); *A61N 2005/0663* (2013.01)

(56) References Cited

OTHER PUBLICATIONS

Photomedicine and Laser Surgery vol. 31, No. 11, 2013, pp. 531-538.
Photomedicine and Laser Surgery vol. 24, No. 6, 2006, pp. 684-688.
Photomedicine and Laser Surgery vol. 33, No. 5, 2015, pp. 278-282.

* cited by examiner

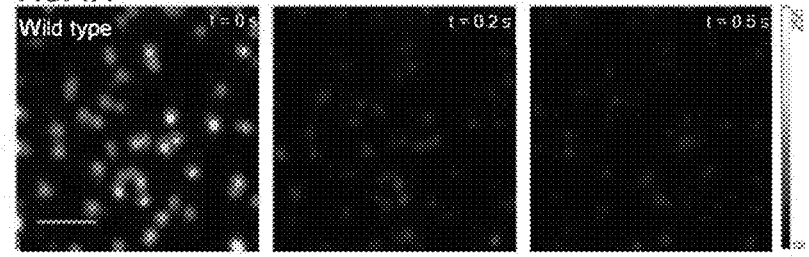
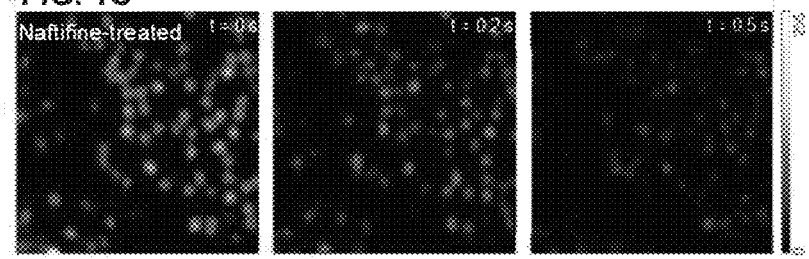
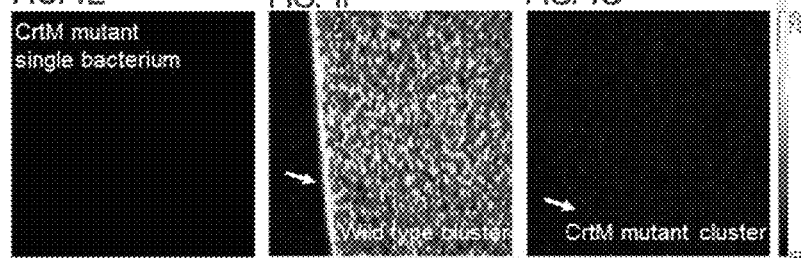
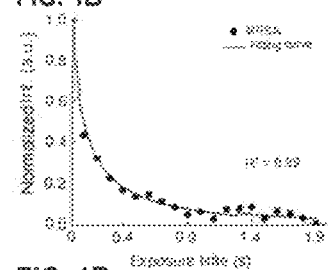
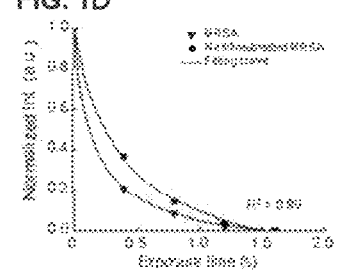
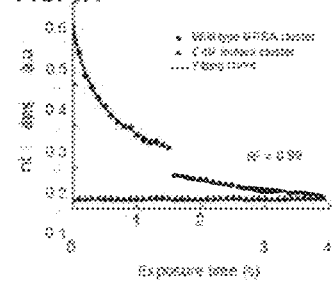

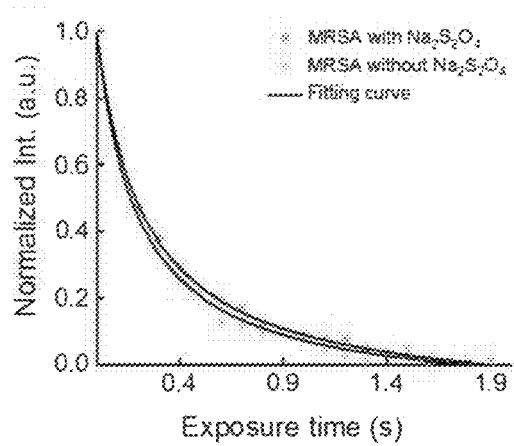
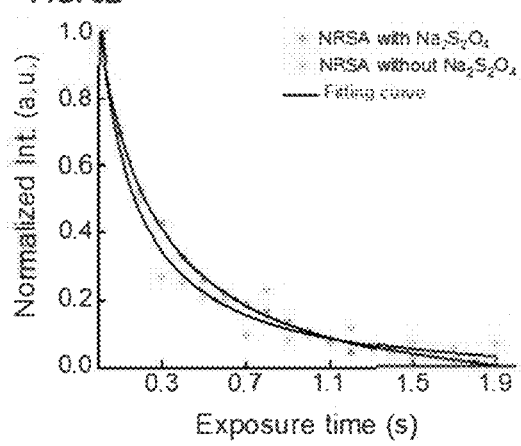

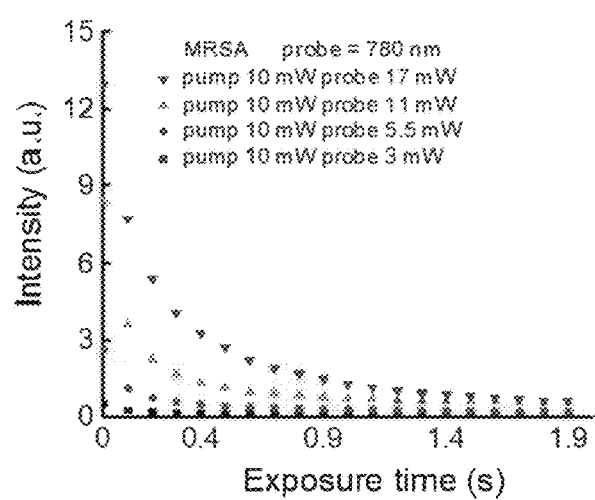
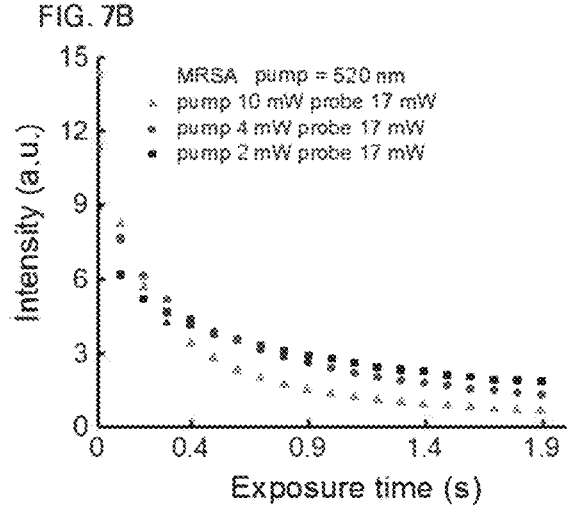

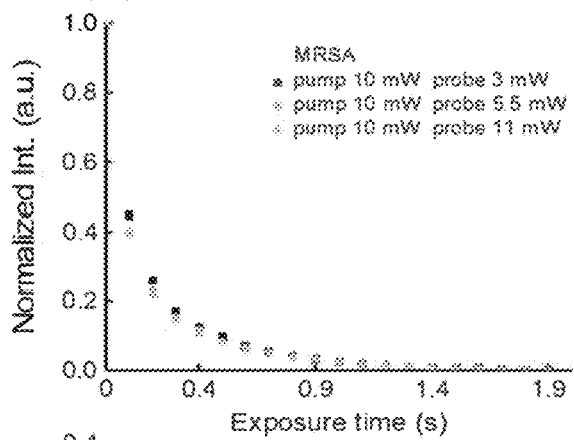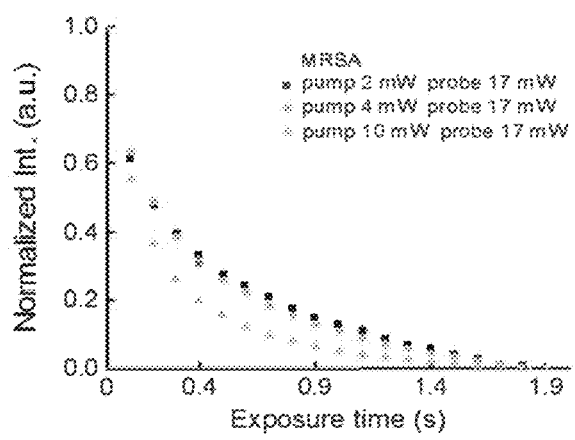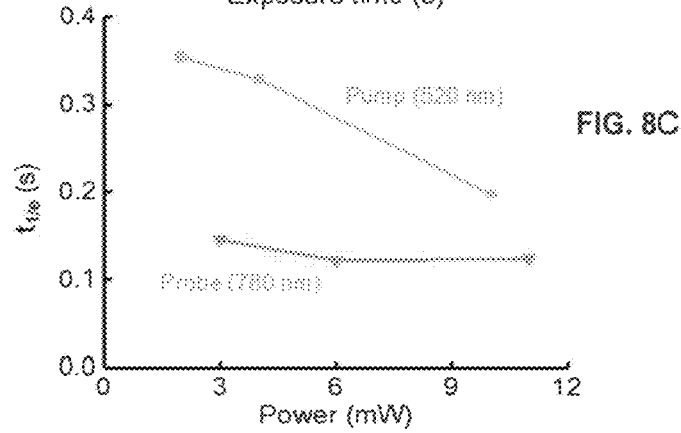

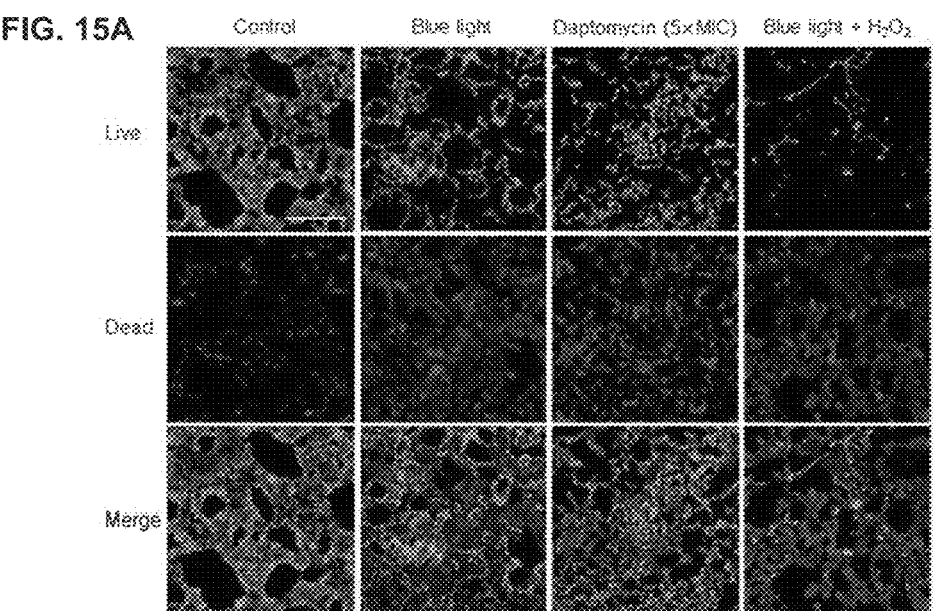
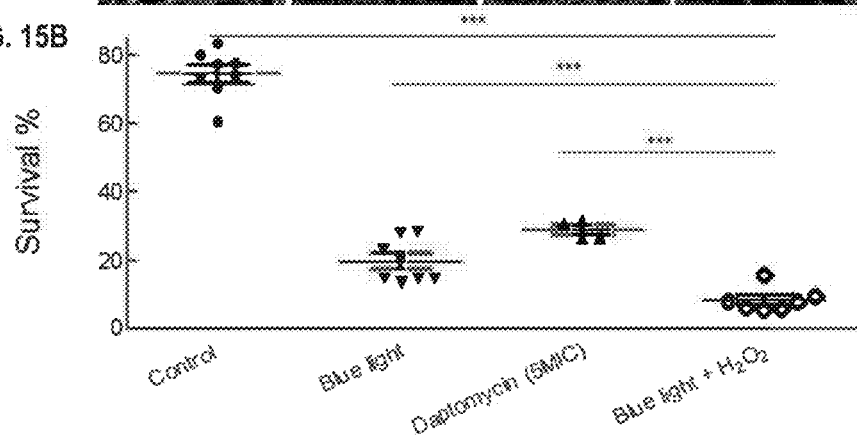

FIG. 17B Cont'd

Table 1. Statistical results of fold change of 200 of cytokines from four different groups. SEM means standard error of mean.

| Groups / Cytokines | Blue light-treated (mean) | Blue light-treated (SEM) | $H_2O_2$-treated (mean) | $H_2O_2$-treated SEM | Fusidic acid-treated (mean) | Fusidic acid-treated (SEM) | Blue light + $H_2O_2$-treated (mean) | Blue light + $H_2O_2$-treated (SEM) |
|---|---|---|---|---|---|---|---|---|
| AR | 0.0253 | 0.0763 | -0.1343 | 0.0330 | 0.6274 | 0.1087 | -0.1069 | 0.0407 |
| Axl | -0.3665 | 0.0116 | -0.1455 | 0.0215 | 0.0523 | 0.0026 | -0.4544 | 0.0135 |
| CD27L | 0.2131 | 0.0643 | 0.1373 | 0.0459 | -0.0491 | 0.0925 | -0.0479 | 0.0727 |
| CD30 | -0.2171 | 0.0572 | -0.0510 | 0.0239 | 0.0137 | 0.0504 | -0.2314 | 0.0749 |
| CD40 | -0.3040 | 0.0331 | -0.1087 | 0.0294 | 0.3337 | 0.0743 | -0.3057 | 0.0519 |
| CXCL16 | 0.2615 | 0.0414 | -0.2162 | 0.0351 | 0.2447 | 0.0692 | -0.1737 | 0.0265 |
| EGF | 0.2468 | 0.0459 | -0.2293 | 0.0651 | 0.0517 | 0.0729 | -0.2807 | 0.0398 |
| E-selectin | -0.1757 | 0.0250 | -0.1083 | 0.0177 | -0.2004 | 0.0209 | -0.4839 | 0.0133 |
| Fractalkine | 0.4714 | 0.1334 | 0.4416 | 0.1303 | -0.2364 | 0.3307 | -0.3121 | 0.2979 |
| GITR | 0.0287 | 0.0995 | -0.1455 | 0.0721 | 0.3956 | 0.0650 | 0.0465 | 0.0672 |
| HGF | 0.3286 | 0.0154 | 0.2749 | 0.0216 | 0.2701 | 0.0221 | 0.2357 | 0.0306 |
| IGFBP-2 | -0.0760 | 0.0183 | 0.0153 | 0.0161 | -0.0879 | 0.0174 | -0.1529 | 0.0262 |
| IGFBP-3 | -0.2336 | 0.0106 | -0.2116 | 0.0150 | -0.2120 | 0.0029 | -0.4210 | 0.0134 |
| IGFBP-5 | -0.1284 | 0.0098 | 0.0442 | 0.0247 | -0.0782 | 0.0200 | -0.1908 | 0.0205 |
| IGFBP-6 | -0.1094 | 0.0025 | -0.2300 | 0.0204 | -0.2697 | 0.0141 | -0.5027 | 0.0202 |
| IGF-1 | 0.0822 | 0.0085 | 0.2487 | 0.0399 | -0.4445 | 0.0034 | -0.3178 | 0.0025 |
| IL-12p70 | 0.0238 | 0.0095 | -0.1362 | 0.0201 | 0.0029 | 0.0236 | -0.0909 | 0.0295 |
| IL-17E | -0.2118 | 0.0335 | -0.3214 | 0.0244 | -0.1800 | 0.0079 | -0.3887 | 0.0604 |
| IL-17F | -0.0032 | 0.0262 | 0.6993 | 0.0530 | 0.2592 | 0.0461 | 0.0647 | 0.0328 |
| IL-1ra | -0.0233 | 0.0048 | 0.1670 | 0.0132 | 0.3851 | 0.0233 | -0.1671 | 0.0095 |
| IL-2 Ra | -0.0725 | 0.0265 | 0.2015 | 0.0391 | 0.1879 | 0.0242 | -0.0608 | 0.0375 |
| IL-20 | -0.1622 | 0.0467 | -0.1274 | 0.0482 | 0.0953 | 0.0715 | -0.1997 | 0.0352 |
| IL-23 | 0.2510 | 0.1121 | 0.1392 | 0.1553 | 0.2627 | 0.1342 | 0.6352 | 0.2227 |
| IL-28 | 0.1631 | 0.0296 | 0.2046 | 0.0485 | -0.1588 | 0.0353 | -0.1617 | 0.0335 |
| I-TAC | -0.0940 | 0.0819 | -0.1457 | 0.1209 | 0.3744 | 0.1874 | -0.0088 | 0.1025 |
| MDC | 0.2800 | 0.0209 | 0.5488 | 0.0762 | -0.0764 | 0.0156 | 0.5404 | 0.0882 |
| MIP-2 | 0.0488 | 0.0222 | -0.0277 | 0.0378 | -0.0070 | 0.0018 | -0.2246 | 0.1166 |

FIG. 17B Cont'd

| | | | | | | | | |
|---|---|---|---|---|---|---|---|---|
| MIP-3a | -0.1213 | 0.0728 | 0.3267 | 0.1251 | 0.3460 | 0.1535 | -0.0532 | 0.0893 |
| OPN | -0.3248 | 0.0228 | -0.2307 | 0.0106 | 0.8216 | 0.0675 | -0.3776 | 0.0194 |
| OPG | -0.0834 | 0.0274 | -0.2142 | 0.0205 | 0.9914 | 0.0447 | -0.1911 | 0.0649 |
| Prolactin | 0.0326 | 0.0264 | 0.2852 | 0.2180 | 0.4580 | 0.2106 | 0.0106 | 0.1234 |
| Pro-MMP-9 | 0.0533 | 0.0035 | 0.0213 | 0.0104 | 0.0197 | 0.0078 | 0.0371 | 0.0119 |
| P-selectin | -0.3221 | 0.0083 | -0.4006 | 0.0040 | -0.2374 | 0.0017 | -0.6809 | 0.0037 |
| Resistin | -0.0653 | 0.0043 | -0.3623 | 0.0086 | 0.2752 | 0.0093 | -0.4256 | 0.0110 |
| SCF | -0.1139 | 0.0489 | 0.1915 | 0.1365 | 0.1498 | 0.1371 | 0.0971 | 0.0282 |
| SDF-1a | -0.0106 | 0.0562 | -0.0807 | 0.0239 | 0.1707 | 0.0490 | 0.0789 | 0.0302 |
| TPO | 0.0443 | 0.0135 | -0.0215 | 0.0373 | 0.2663 | 0.0575 | -0.2020 | 0.0404 |
| VCAM-1 | -0.2367 | 0.0029 | -0.1357 | 0.0117 | -0.0283 | 0.0066 | -0.4501 | 0.0076 |
| VEGF | 0.0143 | 0.0232 | -0.0295 | 0.0258 | 0.0403 | 0.0167 | -0.2100 | 0.0319 |
| VEGF-D | 0.0806 | 0.0440 | -0.0146 | 0.0326 | 0.0367 | 0.0055 | -0.3018 | 0.0227 |
| bFGF | 0.2019 | 0.0951 | -0.2542 | 0.0322 | -0.4981 | 0.0511 | -0.6184 | 0.0076 |
| BLC | -0.5350 | 0.0778 | -0.1960 | 0.0503 | -0.3200 | 0.2049 | -0.4361 | 0.1007 |
| CD30L | -0.0464 | 0.0516 | -0.0733 | 0.0442 | -0.0682 | 0.0819 | -0.1525 | 0.0262 |
| Eotaxin | 0.7177 | 0.3852 | 0.8584 | 0.3304 | 0.8019 | 0.6864 | 0.9933 | 0.7221 |
| Eotaxin-2 | -0.0452 | 0.1538 | -0.5961 | 0.2399 | 0.0292 | 0.0267 | -0.0520 | 0.2651 |
| Fas L | 0.2062 | 0.2190 | -0.2203 | 0.0392 | -0.4112 | 0.1607 | -0.6607 | 0.0141 |
| G-CSF | 0.0729 | 0.0174 | -0.4083 | 0.0165 | 0.1394 | 0.0159 | -0.6434 | 0.0095 |
| GM-CSF | -0.2760 | 0.0372 | -0.1960 | 0.0233 | -0.1708 | 0.0467 | 0.1285 | 0.0466 |
| ICAM-1 | 1.1571 | 0.3613 | -0.0362 | 0.0593 | 1.5512 | 0.0763 | -0.4232 | 0.0112 |
| IFNg | -0.0471 | 0.0315 | -0.2366 | 0.0325 | -0.0599 | 0.0456 | -0.2612 | 0.0433 |
| IL-1a | 0.0649 | 0.0200 | 0.0141 | 0.0258 | -0.0503 | 0.0151 | -0.1406 | 0.0271 |
| IL-1b | -0.1198 | 0.0797 | 0.2075 | 0.0322 | -0.2158 | 0.0442 | 0.2268 | 0.0879 |
| IL-2 | -0.0011 | 0.0608 | -0.1860 | 0.0312 | 0.0606 | 0.0464 | -0.2761 | 0.0298 |
| IL-3 | 0.0171 | 0.0455 | 0.1781 | 0.0131 | 0.1398 | 0.0616 | 0.1911 | 0.0329 |
| IL-4 | -0.1276 | 0.0360 | -0.2011 | 0.0249 | -0.0096 | 0.0534 | -0.3169 | 0.0233 |
| IL-5 | -0.0918 | 0.0720 | -0.3106 | 0.0187 | -0.0953 | 0.0558 | -0.2998 | 0.0513 |
| IL-6 | 0.0085 | 0.0663 | -0.2775 | 0.0467 | 0.2682 | 0.0345 | -0.2068 | 0.0245 |
| IL-7 | -0.1130 | 0.2833 | -0.0083 | 0.4243 | 0.1116 | 0.1899 | -0.1273 | 0.1945 |
| IL-10 | -0.1209 | 0.0256 | -0.1759 | 0.0236 | -0.0351 | 0.0477 | -0.1589 | 0.0408 |
| IL-12p40 | 0.1462 | 0.0502 | 0.0200 | 0.0322 | 0.0324 | 0.0810 | -0.1654 | 0.0628 |

FIG. 17B Cont'd

| | | | | | | | | |
|---|---|---|---|---|---|---|---|---|
| IL-13 | -0.3103 | 0.1384 | -0.4855 | 0.1559 | -0.5654 | 0.2744 | 0.0537 | 0.2934 |
| IL-15 | 0.1103 | 0.1950 | -0.1351 | 0.0599 | -0.0506 | 0.0964 | 0.1134 | 0.1189 |
| IL-17 | -0.1805 | 0.0238 | 1.4006 | 0.1593 | 0.2684 | 0.0368 | -0.2598 | 0.0373 |
| IL-21 | 0.2484 | 0.3366 | -0.5851 | 0.2910 | -0.4052 | 0.2764 | -0.1496 | 0.2755 |
| KC | 0.0887 | 0.0175 | -0.0602 | 0.0226 | 0.0909 | 0.0184 | -0.2108 | 0.0195 |
| Leptin | 0.4501 | 0.0195 | -0.1401 | 0.2313 | -0.1199 | 0.0094 | -0.5289 | 0.0781 |
| LIX | 0.2186 | 0.0849 | -0.2304 | 0.0473 | -0.0313 | 0.0181 | -0.4204 | 0.0192 |
| MCP-1 | 0.2899 | 0.0827 | 0.9431 | 0.0304 | 0.0071 | 0.0722 | 0.3119 | 0.0795 |
| MCP-5 | 0.4730 | 0.1836 | -0.8808 | 0.0331 | -0.0915 | 0.0493 | -0.4174 | 0.2217 |
| MCSF | 0.2029 | 0.0613 | -0.0002 | 0.0172 | -0.5503 | 0.0202 | -0.3853 | 0.0330 |
| MIG | 0.6206 | 0.1996 | -0.1127 | 0.0326 | 0.5378 | 0.1103 | 0.3828 | 0.0517 |
| MIP-1a | 0.1419 | 0.0193 | -0.3107 | 0.0383 | -0.3165 | 0.0278 | -0.6672 | 0.0074 |
| MIP-1g | 0.1167 | 0.0336 | -0.0241 | 0.0197 | 0.0304 | 0.0144 | -0.2576 | 0.0105 |
| PF4 | -0.3297 | 0.1071 | -0.7429 | 0.0304 | -0.6256 | 0.0740 | -0.6165 | 0.1723 |
| RANTES | -0.1383 | 0.2254 | -0.4249 | 0.2078 | -0.2545 | 0.1164 | -0.2548 | 0.1306 |
| TARC | 0.2738 | 0.2655 | -0.4322 | 0.2926 | 0.3205 | 0.1708 | -0.7453 | 0.1122 |
| TCA-3 | -0.2486 | 0.0114 | -0.2756 | 0.0436 | -0.1264 | 0.0578 | -0.2991 | 0.0290 |
| TNF RI | -0.1672 | 0.0122 | -0.2939 | 0.0366 | -0.1306 | 0.0591 | -0.5615 | 0.0318 |
| TNF RII | -0.0452 | 0.0191 | -0.1233 | 0.0203 | -0.2811 | 0.0052 | -0.4056 | 0.0120 |
| TNFα | -0.0792 | 0.0471 | 0.1039 | 0.0407 | -0.4306 | 0.0182 | -0.1717 | 0.0477 |
| 6Ckine | -0.2017 | 0.0536 | -0.3474 | 0.0359 | 0.0930 | 0.0636 | -0.3244 | 0.0782 |
| Activin A | 0.2080 | 0.1248 | 0.0097 | 0.1383 | 0.2305 | 0.1051 | -0.1235 | 0.0752 |
| ADAMTS1 | 0.1622 | 0.0835 | 0.1068 | 0.0187 | 0.2350 | 0.0792 | 0.0183 | 0.0304 |
| Adiponen | -0.0615 | 0.0556 | -0.0278 | 0.0384 | 0.0147 | 0.0119 | -0.0459 | 0.0212 |
| ANG-3 | -0.3493 | 0.0690 | -0.1019 | 0.1171 | 0.0313 | 0.1455 | -0.1613 | 0.0772 |
| ANGPTL3 | -0.4744 | 0.2343 | -0.1222 | 0.1516 | -0.2231 | 0.1000 | -0.2169 | 0.1404 |
| Artemin | 0.0300 | 0.0845 | 0.0433 | 0.0316 | 0.4218 | 0.4931 | 1.0812 | 0.8646 |
| CCL28 | -0.1679 | 0.1123 | -0.6841 | 0.2340 | 1.0791 | 1.3719 | -0.0230 | 0.0453 |
| CD36 | -0.4046 | 0.0415 | -0.4456 | 0.0342 | 0.0674 | 0.0331 | -0.2357 | 0.0421 |
| Chordin | -0.1152 | 0.0448 | -0.0093 | 0.0715 | -0.0599 | 0.0534 | -0.1698 | 0.0453 |
| CRP | -0.1386 | 0.0621 | -0.2262 | 0.0133 | -0.0863 | 0.0390 | -0.6176 | 0.0347 |
| E-Cadherin | -0.0110 | 0.0399 | -0.1379 | 0.0244 | 0.1848 | 0.0312 | -0.0999 | 0.0321 |
| Epigen | -0.1274 | 0.0941 | -0.1588 | 0.0535 | -0.0490 | 0.1059 | -0.0790 | 0.0640 |

FIG. 17B Cont'd

| | | | | | | | | |
|---|---|---|---|---|---|---|---|---|
| Epiregulin | 0.0589 | 0.1819 | -0.2878 | 0.1312 | -0.2220 | 0.1128 | -0.3278 | 0.1062 |
| Fas | -0.1400 | 0.0892 | -0.3001 | 0.0746 | 0.0163 | 0.1182 | -0.1501 | 0.1406 |
| Galectin-7 | -0.3203 | 0.0284 | -0.3150 | 0.0754 | 0.7990 | 0.0420 | -0.2551 | 0.0257 |
| gp130 | -0.0160 | 0.0246 | 0.1048 | 0.2725 | 0.5867 | 0.1372 | -0.3457 | 0.1337 |
| Granzyme B | -0.0904 | 0.0532 | 0.2145 | 0.0347 | 0.5603 | 0.0682 | -0.1550 | 0.0897 |
| Gremlin | -0.5466 | 0.3567 | -0.8057 | 0.1047 | 4.9707 | 2.4157 | -0.6070 | 0.0440 |
| IFNg R1 | -0.2039 | 0.0343 | -0.2832 | 0.0240 | 0.0709 | 0.0445 | -0.2927 | 0.0458 |
| IL-17B | -0.1487 | 0.0974 | -0.2485 | 0.1711 | -0.0513 | 0.1850 | -0.3900 | 0.1458 |
| IL-17B R | -0.0890 | 0.0572 | 0.0438 | 0.2243 | 0.4884 | 0.0727 | 0.0476 | 0.1280 |
| IL-22 | -0.0037 | 0.0483 | -0.5330 | 0.1964 | -0.0487 | 0.0684 | 0.2242 | 0.2403 |
| MIP-1b | -0.1873 | 0.0215 | -0.4967 | 0.0257 | -0.5769 | 0.0187 | -0.8282 | 0.0084 |
| MMP-2 | -0.4581 | 0.0237 | -0.5768 | 0.0277 | 0.1026 | 0.0759 | -0.5532 | 0.0261 |
| MMP-3 | 0.0194 | 0.0341 | -0.0983 | 0.0203 | -0.1230 | 0.0304 | -0.2390 | 0.0512 |
| MMP-10 | 0.1624 | 0.0948 | -0.1476 | 0.0691 | 0.3470 | 0.1412 | -0.1524 | 0.0660 |
| PDGF-AA | -0.1688 | 0.0637 | -0.4666 | 0.0335 | 0.4578 | 0.0075 | -0.3440 | 0.1022 |
| Persephin | -0.0917 | 0.1338 | -0.3386 | 0.0476 | 0.5348 | 0.4577 | -0.3563 | 0.1026 |
| sFRP-3 | 0.1509 | 0.1414 | -0.1892 | 0.0965 | 0.0607 | 0.1143 | -0.1970 | 0.0940 |
| Shh-N | -0.1287 | 0.0334 | -0.1527 | 0.0915 | -0.0849 | 0.0589 | -0.1079 | 0.0621 |
| SLAM | -0.1210 | 0.0730 | -0.0883 | 0.0369 | 0.1871 | 0.1523 | 0.0213 | 0.2118 |
| TCK-1 | -0.2505 | 0.0355 | -0.4843 | 0.0284 | -0.0185 | 0.0460 | -0.5671 | 0.0480 |
| TECK | 0.2380 | 0.1331 | 0.1734 | 0.1356 | 0.4329 | 0.0196 | 0.1942 | 0.2169 |
| TGFb1 | -0.0744 | 0.0333 | -0.1570 | 0.0374 | 0.0743 | 0.0947 | -0.2710 | 0.0161 |
| TRANCE | -0.0561 | 0.0631 | 0.0878 | 0.1184 | 0.0310 | 0.1001 | -0.1081 | 0.0971 |
| TremL1 | -0.2420 | 0.0475 | -0.2695 | 0.0400 | -0.0440 | 0.0605 | -0.3751 | 0.0647 |
| TWEAK | -0.1893 | 0.0429 | -0.1667 | 0.0388 | -0.0621 | 0.0444 | -0.2538 | 0.0509 |
| VEGF-B | -0.0310 | 0.0315 | -0.0693 | 0.0743 | 0.0230 | 0.0936 | -0.1112 | 0.0636 |
| VEGF R2 | -0.1005 | 0.0875 | -0.1809 | 0.1361 | 0.0949 | 0.0795 | -0.1262 | 0.0834 |
| 4-1BB | -0.1530 | 0.0340 | -0.2733 | 0.0387 | -0.0924 | 0.0238 | -0.2811 | 0.0400 |
| ACE | -0.6697 | 0.0088 | -0.8627 | 0.0085 | -0.3271 | 0.0188 | -0.9222 | 0.0040 |
| ALK-1 | -0.0477 | 0.0398 | -0.1821 | 0.0440 | -0.0491 | 0.0488 | -0.1008 | 0.0807 |
| CT-1 | -0.1602 | 0.0470 | -0.3499 | 0.0547 | -0.0581 | 0.0542 | -0.4161 | 0.0616 |
| CD27 | 0.6073 | 0.5536 | 0.1670 | 0.2393 | 0.2818 | 0.4635 | -0.0552 | 0.2504 |
| CD40L | -0.0735 | 0.0299 | -0.2549 | 0.0348 | 0.0244 | 0.0566 | -0.1621 | 0.0480 |

FIG. 17B Cont'd

| | | | | | | | | |
|---|---|---|---|---|---|---|---|---|
| CTLA4 | -0.2401 | 0.0731 | -0.1747 | 0.0381 | 0.2149 | 0.0247 | -0.2247 | 0.0479 |
| Decorin | 0.0408 | 0.0208 | -0.0051 | 0.0142 | -0.0222 | 0.0116 | -0.0389 | 0.0121 |
| Dkk-1 | -0.0611 | 0.1164 | -0.4175 | 0.0776 | 0.1157 | 0.1753 | -0.3092 | 0.0689 |
| Dtk | -0.1949 | 0.1068 | -0.3288 | 0.1031 | 0.1217 | 0.1707 | -0.3991 | 0.1426 |
| Endoglin | -0.6549 | 0.0189 | -0.6896 | 0.0102 | 0.4267 | 0.0442 | -0.8240 | 0.0112 |
| Fcg RIIB | 0.1707 | 0.2691 | 0.2388 | 0.1323 | 0.0602 | 0.1175 | 0.0869 | 0.1740 |
| Flt-3L | -0.2097 | 0.0498 | -0.2615 | 0.0403 | 0.1619 | 0.0536 | -0.4176 | 0.0342 |
| Galectin-1 | -0.2113 | 0.0094 | -0.1195 | 0.0029 | 0.0284 | 0.0165 | -0.2467 | 0.0118 |
| Galectin-3 | 0.0829 | 0.0328 | 0.0550 | 0.0434 | 0.0624 | 0.0393 | -0.0718 | 0.0049 |
| Gas 1 | -0.7289 | 0.0135 | -0.7018 | 0.0130 | 0.0715 | 0.0443 | -0.8007 | 0.0075 |
| Gas 6 | -0.3223 | 0.0735 | -0.3085 | 0.0342 | -0.0661 | 0.1169 | -0.4867 | 0.0492 |
| GITR L | -0.3959 | 0.0856 | -0.0425 | 0.0204 | 0.2327 | 0.2062 | 0.2469 | 0.2119 |
| HAI-1 | 0.1479 | 0.0643 | -0.0794 | 0.0321 | 0.2271 | 0.1224 | -0.0636 | 0.0616 |
| HGF R | 0.0369 | 0.0107 | 0.0240 | 0.0153 | 0.0292 | 0.0500 | -0.1031 | 0.0468 |
| IL-1 R4 | -0.2815 | 0.1231 | 0.0090 | 0.0505 | -0.0208 | 0.1191 | -0.3740 | 0.0468 |
| IL-3 Rb | 0.0853 | 0.0438 | -0.0953 | 0.0536 | 0.0789 | 0.0915 | -0.1247 | 0.0511 |
| IL-9 | 0.1911 | 0.0691 | 0.0482 | 0.0506 | 0.1408 | 0.0456 | -0.0427 | 0.0813 |
| JAM-A | -0.4151 | 0.0115 | -0.2998 | 0.0142 | 0.3062 | 0.0168 | -0.3706 | 0.0141 |
| Leptin R | 0.1395 | 0.0794 | -0.1563 | 0.0080 | 0.1134 | 0.0633 | -0.0508 | 0.0493 |
| L-Selectin | -0.0584 | 0.0108 | -0.1755 | 0.0156 | -0.3559 | 0.0035 | -0.4079 | 0.0735 |
| Lymphotactin | 0.1433 | 0.0601 | 0.0191 | 0.0046 | 0.0906 | 0.0649 | -0.0217 | -0.0040 |
| MadCAM-1 | -0.0329 | 0.0944 | -0.3032 | -0.1074 | -0.0787 | 0.0310 | -0.3479 | -0.0915 |
| MFG-E8 | -0.1803 | 0.0985 | -0.1414 | 0.1428 | 0.4647 | 0.1403 | -0.2667 | 0.1627 |
| MIP-3b | -0.2876 | 0.0513 | -0.1993 | 0.0255 | 0.0690 | 0.0673 | -0.2626 | 0.0466 |
| Neprilysin | -0.1241 | 0.0550 | -0.2555 | 0.0249 | 0.5936 | 0.0602 | -0.1471 | 0.0492 |
| Pentraxin 3 | -0.7139 | 0.0144 | -0.7179 | 0.0093 | -0.6735 | 0.0176 | -0.7512 | 0.0104 |
| RAGE | 0.8636 | 0.2700 | -0.0350 | 0.1165 | 0.1727 | 0.2876 | 0.4286 | 0.2164 |
| TACI | 0.5432 | 0.2929 | -0.2636 | 0.0362 | 0.4640 | 0.1721 | -0.3018 | 0.0360 |
| TREM-1 | 0.0515 | 0.0298 | 0.0703 | 0.0184 | 0.0981 | 0.0315 | 0.0117 | 0.0077 |
| TROY | -0.1253 | 0.0410 | -0.0721 | 0.0387 | 0.0517 | 0.0974 | -0.1897 | 0.0562 |
| TSLP | 0.0850 | 0.0151 | -0.1726 | 0.0151 | -0.0086 | 0.0330 | -0.1796 | 0.0443 |
| TWEAK R | -0.4665 | 0.0161 | -0.4445 | 0.0379 | -0.2341 | 0.0367 | -0.5804 | 0.0194 |
| VEGF R1 | -0.1990 | 0.0149 | -0.4184 | 0.0362 | 0.1580 | 0.0664 | -0.4483 | 0.0338 |

FIG. 17B Cont'd

| | | | | | | | | |
|---|---|---|---|---|---|---|---|---|
| VEGF R3 | 0.0627 | 0.0449 | -0.0705 | 0.0214 | 0.1061 | 0.0391 | -0.1200 | 0.0387 |
| B7-1 | 0.0247 | 0.0148 | 0.2808 | 0.0332 | -0.0661 | 0.0583 | -0.4049 | 0.0401 |
| BAFF R | 0.0229 | 0.1585 | 0.0988 | 0.0509 | 0.0687 | 0.1658 | 0.2564 | 0.2350 |
| BTC | 2.0760 | 0.4898 | 0.9018 | 0.0595 | 3.8576 | 0.5841 | 0.4695 | 0.2331 |
| C5a | 0.0615 | 0.0256 | 0.1618 | 0.0348 | 0.1215 | 0.0296 | -0.0793 | 0.0290 |
| CCL6 | -0.2209 | 0.0121 | -0.3559 | 0.0061 | -0.4027 | 0.0195 | -0.7546 | 0.0079 |
| CD48 | -0.5379 | 0.0303 | -0.3656 | 0.0460 | -0.0498 | 0.0649 | -0.4659 | 0.0151 |
| CD6 | -0.4826 | 0.0247 | -0.2795 | 0.1299 | 0.3476 | 0.3088 | -0.4601 | 0.0168 |
| Chemerin | 0.0599 | 0.0631 | -0.2510 | 0.1370 | 0.1948 | 0.2769 | -0.3033 | 0.2422 |
| Clusterin | -0.0664 | 0.0213 | 0.1123 | 0.0413 | 0.2455 | 0.0152 | -0.0353 | 0.0350 |
| Lungkine | -0.0667 | 0.0931 | -0.0954 | 0.0345 | -0.0819 | 0.0373 | -0.0777 | 0.0789 |
| Cystatin C DAN | -0.0737 | 0.0245 | 0.0313 | 0.0278 | -0.0271 | 0.0133 | 0.0283 | 0.0171 |
| DLL4 | -0.1527 | 0.0099 | -0.0364 | 0.0433 | -0.0252 | 0.0551 | -0.1180 | 0.0203 |
| EDAR | 0.0980 | 0.0929 | 0.0841 | 0.0730 | -0.4592 | 0.2757 | 0.0023 | 0.0758 |
| Endocan | -0.3661 | 0.0901 | -0.0335 | 0.0915 | 0.0559 | 0.2286 | -0.5513 | 0.0921 |
| Fetuin A | -0.7771 | 0.0143 | -0.5133 | 0.0105 | -0.6614 | 0.0123 | -0.5076 | 0.0397 |
| H60 | 0.3941 | 0.2064 | -0.0250 | 0.2394 | 0.2171 | 0.1074 | -0.6484 | 0.2325 |
| IL-33 | -0.6506 | 0.0773 | -0.6370 | 0.0229 | 0.3416 | 0.0791 | -0.6861 | 0.0293 |
| IL-7 Ra | -0.3610 | 0.2570 | -0.4620 | 0.2010 | -0.7276 | 0.2177 | -0.8567 | 0.1241 |
| Kremen-1 | 0.0957 | 0.0261 | -0.4332 | 0.2739 | 0.2672 | 0.2121 | 0.0365 | 0.0424 |
| Limitin | 0.6721 | 0.3043 | 0.5441 | 0.2060 | -0.1844 | 0.3041 | 0.0561 | 0.0536 |
| Lipocalin-2 | -0.1402 | 0.0213 | -0.0669 | 0.0120 | -0.0695 | 0.0215 | -0.2269 | 0.1060 |
| LOX-1 | 0.0330 | 0.0189 | 0.0229 | 0.0122 | 0.0568 | 0.0316 | 0.0374 | 0.0218 |
| Marapsin | -0.3802 | 0.1087 | -0.0476 | 0.0430 | -0.1703 | 0.1764 | -0.4160 | 0.1584 |
| MBL-2 | -0.1568 | 0.0559 | -0.0587 | 0.1046 | 0.0693 | 0.0575 | -0.0253 | 0.1203 |
| Meteorin | 0.2441 | 0.2360 | 0.4960 | 0.1991 | 0.3361 | 0.2009 | 0.3874 | 0.1863 |
| Nope | -0.3388 | 0.0519 | -0.2914 | 0.0262 | 0.0534 | 0.0190 | -0.4400 | 0.0125 |
| NOV | -0.3379 | 0.2091 | -0.1756 | 0.0318 | -0.2053 | 0.1403 | -0.9702 | 0.0258 |
| Osteoactivin | -0.2787 | 0.1389 | 0.4709 | 0.2336 | 1.1132 | 0.3224 | 0.4250 | 0.1957 |
| OX40 Ligand | -0.2417 | 0.1367 | 0.2366 | 0.2572 | -0.1454 | 0.3266 | -0.3974 | 0.0926 |
| P-Cadherin | -0.4885 | 0.0090 | -0.0660 | 0.0326 | 0.5883 | 0.0546 | -0.1158 | 0.0448 |
| Periostin | -0.5653 | 0.0135 | -0.5519 | 0.0280 | 0.1651 | 0.0640 | -0.5594 | 0.0138 |

FIG. 17B Cont'd

| | | | | | | | | |
|---|---|---|---|---|---|---|---|---|
| PIGF-2 | -0.2314 | 0.0226 | -0.0738 | 0.0353 | -0.0798 | 0.0662 | -0.2486 | 0.0226 |
| Progranulin | -0.5637 | 0.0105 | -0.6229 | 0.0116 | -0.4424 | 0.0276 | -0.7865 | 0.0108 |
| Prostasin | -0.0635 | 0.0795 | 1.1226 | 0.2206 | 0.1030 | 0.0963 | -0.2391 | 0.2142 |
| Renin 1 | -0.5961 | 0.0248 | -0.3457 | 0.0444 | -0.4138 | 0.0163 | -0.6316 | 0.0220 |
| Testican 3 | -0.5810 | 0.2198 | -0.1883 | 0.1057 | -0.4097 | 0.0586 | -0.6049 | 0.1959 |
| TIM-1 | -0.1186 | 0.0586 | -0.1106 | 0.0563 | -0.0806 | 0.0293 | -0.1534 | 0.0832 |
| Tryptase ε | 0.0853 | 0.1731 | 0.3620 | 0.3840 | -0.0627 | 0.1395 | -0.2941 | 0.2140 |

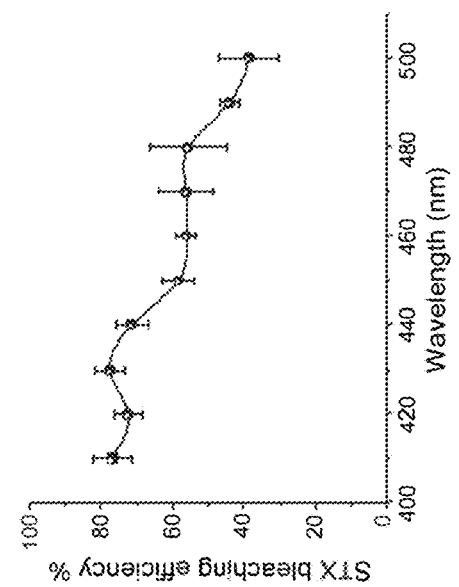
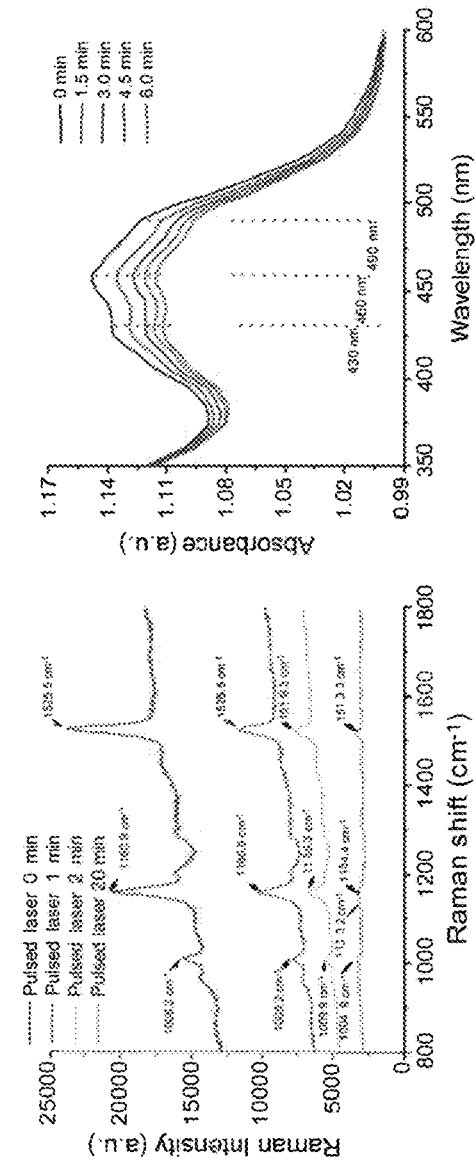
FIG. 19A
FIG. 19B
FIG. 19C

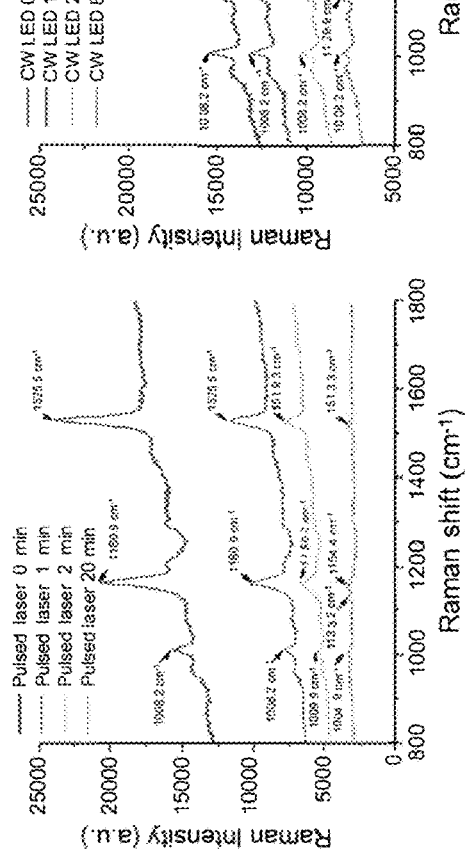

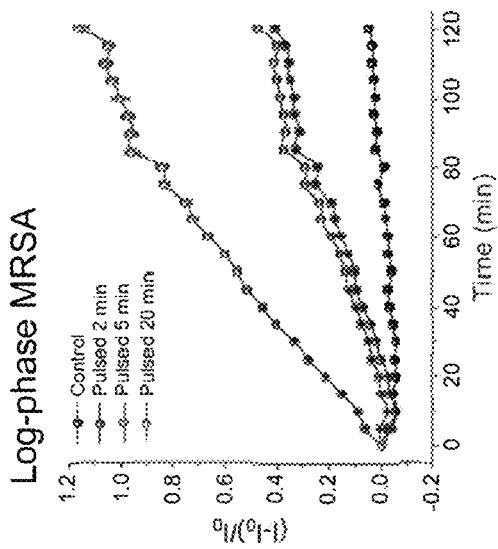
FIG. 23A
FIG. 23B
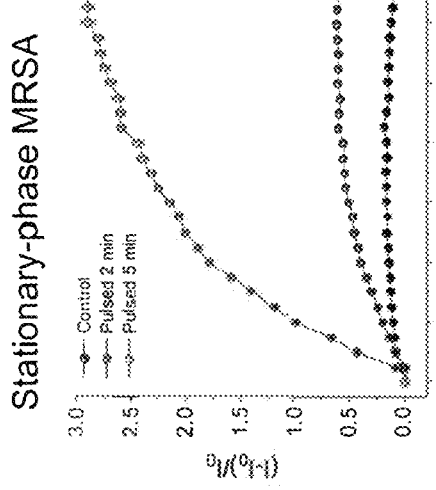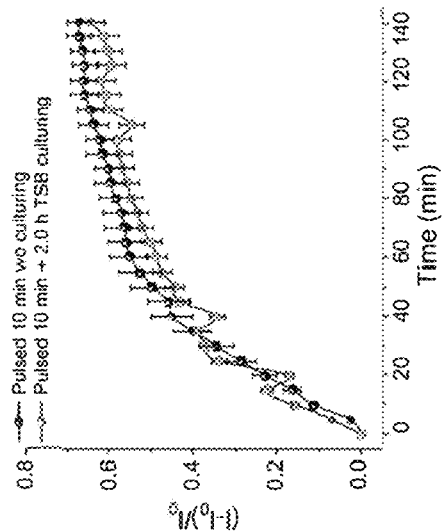
FIG. 23C
All measurement performed in water

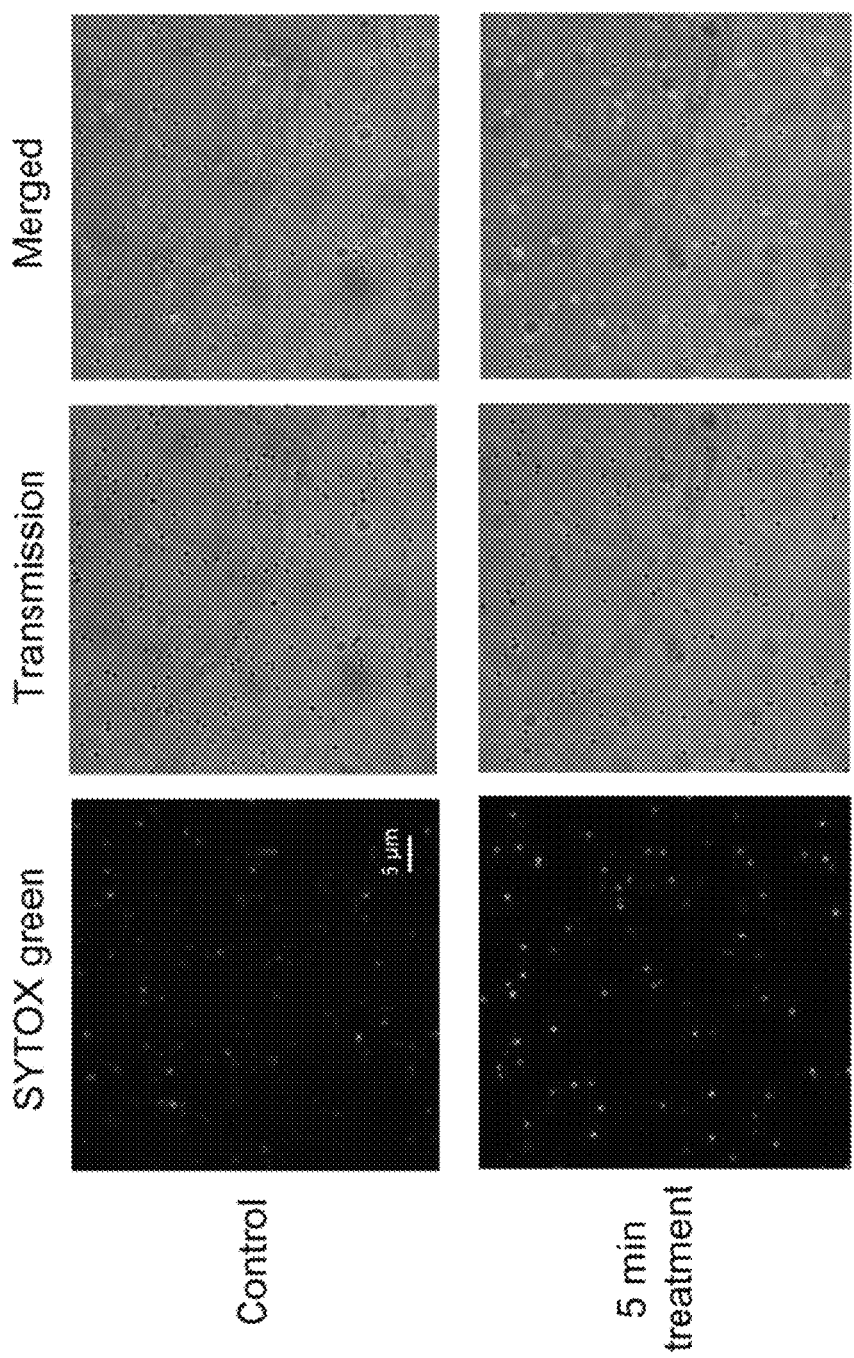

METHOD AND DEVICE FOR ANNIHILATION OF METHICILLIN-RESISTANT *STAPHYLOCOCCUS AUREUS*

FIELD OF INVENTION

This disclosure relates to a novel approach of annihilation of methicillin-resistant *Staphylococcus aureus* (MRSA) via staphyloxanthin (STX) photobleaching. Specifically, it discloses a combination use of antibiotics or hydrogen peroxide or other oxidative agents with appropriate light source to kill MRSA.

BACKGROUND

*Staphylococcus aureus* is a major source of bacterial infections and causes severe health problem in both hospital and community settings (1, 2). Of note, *S. aureus* becomes life-threatening especially when serious infections such as sepsis or necrotizing pneumonia occur (3). Though numerous antibiotics were once effective at treating these infections, *S. aureus* has acquired resistance which diminished the effectiveness of several classes of antibiotics (4). A classic example was the emergence of clinical isolates of MRSA strains in the 1960s that exhibited resistance to f-lactam antibiotics (5-7). More recently, strains of MRSA have manifested reduced susceptibility to new antibiotics and therapeutics such as vancomycin and daptomycin (8, 9). Faced with the severe situation that introduction of new antibiotics into clinic could not keep pace with the rapid development of resistance (4), both the drug industry and health organizations are calling for alternative ways to combat the MRSA resistance.

SUMMARY OF THE INVENTION

This disclosure provides method and device of eradicating methicillin-resistant *Staphylococcus aureus* (MRSA). The method comprising providing pulsed laser or low-level blue lights to MRSA culture, wherein the pulsed laser or low level blue lights create nano-scale pores on functional membrane microdomains of MRSA culture.

In some embodiment, the aforementioned no-delay two laser beams are about 520 nm pump and about 780 nm probe pulses.

In some embodiment, the aforementioned pulsed laser or low-level blue light unanchors PBP2a proteins within the functional membrane microdomains of MRSA culture.

This disclosure further contemplates a portable laser or blue light LED device to provide pulsed laser or low-level blue lights to MRSA culture. The device will contain at least one light source that causes photolysis of STX. In some embodiment the light source has a wavelength of 460 nm or a wavelength within the entire blue light range. In some other embodiment, the device comprising has 8 mm beam size and about 120 mW laser power.

In some embodiment, the aforementioned pulsed laser or blue light LED device further comprises means to spray effective amount of oxidative agent to MRSA culture.

In some embodiment, the aforementioned pulsed laser or blue light LED device is for use to treat skin wound in a subject, for example, in human or in an animal.

In some embodiment, the aforementioned sensitizing method further comprising administering a low-concentration oxidative agent to the MRSA culture. For example, the low-concentration oxidative agent may be hydrogen peroxide.

This disclosure further provides a method of annihilating of MRSA in a patient. The method comprising providing pulsed laser or low-level blue lights and administering effective amounts of oxidative agent to the patient's MRSA infection site.

In some embodiment, the aforementioned pulsed laser or low-level blue lights and oxidative agent are given at the same time or sequentially.

In some embodiment, the aforementioned pulsed laser or low-level blue lights are given before the administering of oxidative agent to MRSA culture.

In some embodiment, the aforementioned patient has an ear infection, a nose infection, or an eye infection.

In some embodiment, the aforementioned patient has skin wound, diabetic ulceration, urinary track infection, bloodstream infection.

In some embodiment, the aforementioned patient has acne.

This disclosure further provides a treatment regimen for treating MRSA infection in a patient. The regimen comprising providing to the patient infection site pulsed laser light or low-level blue lights for a period of time, and administering to the patient an effective amount of antibiotics.

In some preferred embodiment, the aforementioned effective amount of antibiotics is selected from the group consisting of cefotaxime, gentamicin, ciprofloxacin, oxacillin, and daptomycin.

In some preferred embodiment, the aforementioned pulsed laser light or low-level blue light in the treatment regimen is applied to the infection site between about 2 min to about 10 min and has no photo-toxicity to the patient.

These and other features, aspects and advantages of the present invention will become better understood with reference to the following figures, associated descriptions and claims.

BRIEF DESCRIPTION OF THE DRAWINGS

FIG. 1. Photobleaching signature of MRSA under transient absorption microscopy. (FIG. 1A). Time-lapse images of wild-type MRSA. Scalar bar=5 µm. Image acquisition time: 0.1 s. (FIG. 1B). Normalized time-course decreasing curve from wild-type MRSA. (FIG. 1C). Time-lapse images of naftifine-treated MRSA. (FIG. 1D). Normalized time-course curve from wild-type and naftifine-treated MRSA. (FIG. 1E). Image of CrtM mutant (t=0 s). (FIG. 1F-G). Image of wild-type MRSA cluster (t=0 s, FIG. 1F) and CrtM mutant cluster (t=0 s, FIG. 1G). (FIG. 1H). Time-course curve from wild-type cluster (FIG. 1F) and CrtM mutant cluster (FIG. 1G). White arrow: the interface between air and sample. Curve fitted by equation (1).

FIG. 2. Mass spectrometry unveils the photochemistry of STX under blue lght exposure. (FIG. 2H). Annihilation of STX ([M+Na$^+$]) under blue light exposure. (FIG. 2I). Corresponding generation of a representative product during the photobleaching process of STX.

FIG. 3. Blue light and $H_2O_2$ synergistically eliminate MRSA in vitro.

FIG. 4. Blue light and $H_2O_2$ synergistically heal the MRSA-infected mice wound.

FIG. 6. Oxygen dependence upon the photobleaching rate of *S. aureus*. (FIG. 6A). Time-course curves of MRSA with or without $Na_2S_2O_4$. $Na_2S_2O_4$, an oxygen scavenger. (FIG. 6B). Time-course curves of NRSA with or without $Na_2S_2O_4$.

FIG. 7. Power dependence upon the signal intensity of *S. aureus* cluster under pump probe microscopy. Time-lapse curves of MRSA cluster towards probe intensity (FIG. 7A), and pump intensity (FIG. 7B).

FIG. 8. Power dependence upon the photobleaching rate of *S. aureus* cluster under pump probe microscopy. Normalized time-lapse curves of MRSA cluster towards probe intensity (FIG. 8A), and pump intensity (FIG. 8B). (FIG. 8C). The power dependence of the time-course decay of MRSA upon the time spent to reach $$\frac{1}{e} * \text{Intensity}.$$

FIG. 15. Blue light and $H_2O_2$ synergistically scavenge *S. aureus* inside biofilm. (FIG. 15A). Fluorescence imaging of live *S. aureus* (Green, top), dead *S. aureus* (Red, middle) and merged live/dead *S. aureus* (Bottom) inside the biofilms of control group (left lane), Blue light-treated group (left middle), daptomycin-treated group (right middle lane) and blue light+$H_2O_2$-treated group (right lane). A live/dead viability kit was used to stain the cells inside the biofilms. Live: SYTO®9. Dead: Propidium iodide. Scalar bar=10 μm. Blue light: 30-min exposure, 360 J/cm$^2$. $H_2O_2$:13.2 mM, 20-min culture time, then quenched by 0.5 mg/mL catalase solution. (FIG. 15B). Statistical analysis of survival percent of *S. aureus* inside the biofilms at different groups. Survival %=$N_{green}/(N_{green}+N_{red})·N_{green}$ and $N_{red}$ represents the number of live *S. aureus* and dead *S. aureus*, respectively. Data are means (black) with standard error of mean (red). N=7-8, which was chosen from 7-8 different regions of interest, for each region, the size is the same as the image shown in (FIG. 15A).

FIG. 18. Nanosecond pulsed laser would enable dramatically improved STX photolysis efficiency, speed, and depth.

FIG. 19. Quantification of STX photolysis efficiency. Resonance Raman spectroscopy was applied to quantify STX in MRSA and to find the optimal wavelength for photolysis of STX. (FIG. 19A) Raman spectra of MRSA solution under different nanosecond pulsed laser exposure time. STX shows strong Raman signal at ~1008, ~1161, and ~1528 $cm^{-1}$ and the amplitude of these peaks drop dramatically over time. As Raman signal intensity linearly depends on local STX concentration, Raman peak amplitude at 1161 $cm^{-1}$ was used for quantification of STX photolysis efficiency. (FIG. 19B) Absorption spectrums of MRSA solution with different exposure time. Absorption peak drops dramatically with nanosecond laser treatment time, which confirms the Raman spectroscopic study. (C) STX photolysis efficiency at different wavelength with same optical power and dosage (50 mW for 10 min exposure time). STX is effectively bleached within the entire blue light range.

FIG. 20. STX photolysis efficiency, and speed by nanosecond pulsed laser compared with CW LED under the same power. Experiment conducted on MRSA solution sandwiched between two cover glass slides with ~80 μm thickness. Raman spectra of MRSA solution under different nanosecond pulsed laser exposure time (FIG. 20A) and CW LED exposure time (FIG. 20B). Signal drops both by nanosecond pulsed laser and CW LED. (C) STX photolysis efficiency over treatment time for nanosecond pulsed laser and CW LED indicates that pulsed laser is dramatically faster than CW LED in terms of photolysis efficiency and speed. It takes pulsed laser only 4 minutes to bleach more than 80% of STX in MRSA cells, while CW LED needs more than one hour. Even after long treatment, there is still large portion of STX left unbleached by CW LED, but pulsed laser enables nearly complete photolysis.

FIG. 21. With same dosage and same power, pulsed laser enables ~5 fold improvement on treatment depth within one cell cycle treatment time. MRSA solution was treated with pulsed laser or CW LED over real tissue sample with different thickness, and their Raman signal amplitude at 1161 $cm^{-1}$ was then measured over different treatment time. Within one cell cycle treatment time, CW LED barely penetrates 300 um for 50% STX photolysis. While pulsed laser could reach 1 mm with more than 50% STX bleached.

FIG. 22. Resonance Raman spectroscopy to show photochemistry of STX. New Raman peaks shows up at 1133 $cm^{-1}$. A significant blue shift is observed at all three characteristic Raman peaks for STX. Up to 3, 6, 12 $cm^{-1}$ for peaks at ~1008, ~1161, and ~1528 $cm^{-1}$, respectively. These are also the evidences for photochemistry of STX.

FIG. 23. SYTOX green study indicates dramatically improved membrane permeability induced by STX photolysis. Florescence intensity from stationary-phase (FIG. 23A) and log-phase (FIG. 23B) MRSA cells co-cultured within SYTOX green solution monitored in real time. For stationary-phase MRSA, its control groups has no obvious change in fluorescence intensity; while once MRSA cells are treated with pulsed laser, SYTOX green dye can diffuse into the cells, bind to nucleic acids, and then express significantly larger fluorescence intensity. This means that laser treatment damages cell membrane integrity and induces significantly improved permeability to small molecules. Longer treatment time gives us, more bleached STX and more damaged cell membrane. For log-phase cells with less STX on cell membrane, we see smaller fluorescence intensity and slower intracellular diffusion. (FIG. 23C) Florescence intensity from stationary-phase MRSA cells co-cultured within SYTOX green solution monitored in real time (before measurement, MRSA cells are treated with/without 2 hour culturing in nutritious medium). The same intracellular diffusion behavior indicates that MRSA cells could not be able to recover even after two hours culturing in nutritious medium. This means cell membrane is damaged by STX photolysis. The more STX in cell membrane, cell membrane is more severely damaged after light treatment. Also cell membrane cannot be easily recovered after laser treatment.

FIG. 24. SYTOX green confocal laser scanning microscopy to confirm compromised cell membrane integrity induced by STX photolysis. The three columns are SYTOX green fluorescence images, transmission image, and merged images. The first row is acquired from control group. The second row is from 5 min pulsed laser-treated group. We can see significantly larger fluorescence intensity from cells in treated group and the relative percentage of cells that has high fluorescence intensity is also significantly increased. These imaging results confirm that SYTOX green is indeed diffused into the cells.

FIG. 25. Molecular structure of FITC-dextran, used extensively to study cell permeability and cell poration. The molecular weight/size of FITC dextran is controllable in a wide range, with approximate stokes' radii as following:

| | |
|---|---|
| MW 4,000 | Approx. 14 Angstroms |
| MW 10,000 | Approx. 23 Angstroms |
| MW 20,000 | Approx. 33 Angstroms |
| MW 40,000 | Approx. 45 Angstroms |
| MW 70,000 | Approx. 60 Angstroms |
| MW 150,000 | Approx. 65 Angstroms |

FIG. 26. Quantification of membrane poration created via photolysis of STX using FITC-dextran. Intracellular diffusion of FITC-dextran is applied as a model to estimate membrane pore size induced by laser treatment. Fluorescence intensity measured from all MRSA cells after FD70 co-culturing. 2 min laser treatment good enough to induce intercellular diffusion of FD70 with molecular weight of 70K and Stokes radius of 6 nm. 5 min treatment could dramatically intracellular diffusion of FD70. This indicates that membrane pore of 10 nm level has been created via STX photolysis.

FIG. 27. Quantification of membrane poration created via photolysis of STX using FITC-dextran: structured illumination microscopy (SIM) imaging. (FIG. 27A) SIM images of control group and 5 min treated group co-cultured with FD70 and FD500, respectively. (FIG. 27B) Fluorescence intensity measured from all MRSA cells after FD70 and FD500 co-culturing, respectively. Compared with untreated group of FD 70k, 5 min treated group showed significantly higher fluorescence intensity indicating dramatically increased intracellular diffusion of FD70. We then further increased the FITC-dextran molecular weight to **500*k*** with Stokes radii of ~15 nm. But we didn't see significant increased intracellular diffusion. With these results, we can conclude that membrane pores created via STX photolysis can be up to ~10 nm-level size, but smaller than 30 nm. These pores are large enough for nearly every antibiotics target intracellular activity (even for nanoparticle).

FIG. 28. Intracellular diffusion of small-molecule antibiotics gentamicin. Gentamicin was conjugated with a dye, Texas red, so that intracellular gentamicin uptake can be tracked by confocal laser scanning microscopy. This first column is fluorescence channel; the second one is transmission; and the third one is merged image. The first row is acquired from control group and the second row acquired from 5 min treated group. Compared with control group, 5 min treated group shows significantly increased amount of gentamicin inside MRSA cells. This result is further confirmed by fluorescence intensity from entire MRSA volume measured by plate reader. These results indicate that significantly increased cellular uptake of gentamicin can be achieved through large membrane pores created via laser treatment.

(FIG. 30A) Confocal laser scanning microscopy of PBP2a on MRSA cells with/without laser treatment. Consistent with structured illumination microscopic images, in confocal images, significant fluorescence signal drop is observed from cells after laser treatment. (FIG. 30B) Statistical analysis of fluorescence signal from 300 cells from (FIG. 30A) indicates that laser treatment could remove or unanchor a significant portion of PBP2a from cell membrane.

FIG. 31. MRSA with compromised membrane after laser treatment is able to recover in a time dependent manner. Pulsed laser was used to treat stationary-phase MRSA with different time.

Figure 2A:
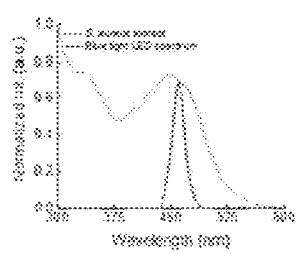
(FIG. 2A). Absorption spectrum of *S. aureus* extract along with the spectrum profile (blue) of blue light LED.

TABLE 1. Statistical results of fold change of 200 of cytokines from four different groups.

SEM means standard error of mean.

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

Superbug infection has become a great threat on global heath, as the pace of resistance acquisition is faster than the clinical introduction of new antibiotics. Consider this reason, WHO listed top 12 superbugs that poses the greatest threat to human health. MRSA is one of them. Our research is focusing on this superbug and using photo-disseambly of membrane microdomains to revive a broad spectrum of antibiotics against MRSA.

There are a variety of disease that are caused by S. aureus or MRSA infection. These can be skin and soft tissue infection, wound infection, diabetic ulceration and sepsis. No matter what kind of disease, once infected by S. aureus or MRSA, routine antibiotics treatment is applied to these infections.

However, S. aureus has various strategies to develop antibiotics resistance. Hence there is a battle between S. aureus evolution and antibiotics development. There are some major defense strategies of S. aureus. First, S. aureus can develop and secrete new enzymes to deactivate antibiotics. For example, beta-lactamase can break the structure of beta-lactamase susceptible beta-lactam antibiotics. Second, they can also change the target of antibiotics. For example, *S. aureus* can generates PBP2a proteins for cell wall synthesis when other PBPs are deactivated by beta-lactam antibiotics. Third, they can pump out antibiotics to reduce intracellular concentration that target intracellular activities, e.g. fluoroquinolones that inhibit DNA synthesis and tetracycline that inhibit RNA activity. Fourth, they can trap antibiotics and make them less active. Or they can acquire resistance through other genetic mutations. Besides resistance development, *S. aureus* can also develop other strategies. They can hide inside host cells, forming biofilms or become persisters that are metabolically inactive thus can tolerant high concentration antibiotics. In recently years, persisters have drawn more and more attentions, as they are particularly responsible for chronic/recurrent infections that are hard to treat in the clinic.

Due to these resistance development strategies, the discovery of novel antibiotics is currently not keeping pace with the emergence of new superbug. Nearly every existing antibiotic has found their resistant strain and the last new antibiotic was clinically introduced 33 years ago. There are multiple reasons for this. Firstly, antibiotics mis-use or overuse on human and livestock. Secondly, it normally takes roughly 10 years to develop a new antibiotic. Third, resistant strains will be soon found for new antibiotics just after a few years. So pharmaceutical companies cannot justify to develop new antibiotics. But still health organizations are calling for novel antibiotics or alternative approaches to combat superbug infections.

There are a few emerging antibiotics or new strategies to treat *S. aurous* infections. Nature 556, 103-107 (2018) by Eleftherios Mylonakis Group demonstrates that synthetic retinoid antibiotics can be developed as new antibiotics to kill MRSA by disrupting their membrane lipid bilayer. These antibiotics also work synergistically with gentamicin due to the disrupted membrane. As another example, Nature 473, 216-220 (2011) by James Collins group demonstrated that some specific metabolic stimuli (e.g. mannitol or glucose) that can generate proton motive force to enable trans-membrane uptake of aminoglycoside antibiotics to kill MRSA persisters. These two strategies highlight the importance of intracellular delivery of antibiotics. This can be done either by disrupting cell membrane or using metabolic stimuli.

Another example is to repurpose existing drug. Cell 171, 1354 (2017) by Danile Lopez Group demonstrates that cholesterol lowering drug, statin, can be used to reduce STX derived lipids within membrane microdomains, thus interferes PBP2a oligomerization and inhibit MRSA penicillin resistance. The paper introduced the concept of functional membrane microdomains (FMM). STX-derived lipids are the constituent lipids for FMM. Flotillins are the scaffold protein within the FMM. Many protein cargoes (e.g. PBP2a) are anchored and oligomerized within FMM. Once treated with statin, STX-derived lipids will be dramatically reduced. Therefore, PBP2a complex will be disassembled and its expressing amount is reduced, so penicillin resistance can be inhibited. Without being limited by any theory, it is proposed that STX is the constituent lipid for FMM and it is highly concentrated within FMM. PBP2a complex is within STX-enriched FMM.

These examples all have the potential to be used in the clinic. However, all these approaches still rely on new drugs or stimuli. *S. aureus* still can potentially develop resistance to these approaches. Also, drugs, e.g. statin, takes long time to make MRSA susceptible to beta-lactam antibiotics.

This disclosure started with an initial unexpected discovery that STX is prone to bleaching by blue light. We accidentally found the photobleaching phenomena on MRSA under transient absorption microscope. FIG. 1 shows transient absorption signal from MRSA dropped dramatically over time with zero delay between pump and probe pulses. To understand which chromophore is responsible for photobleaching, we treated MRSA cells with a FDA-approved drug to block the biosynthesis of STX. We observed a significantly smaller signal intensity and slower photobleaching decay compared to control group. For *S. aureus* mutant, there is no detectable signal. So, here we found that the gold pigment, STX is identified to be responsible for the observed photobleaching. FIG. 2 presents the absorption spectrum of STX and a continuous-wave (CW) LED for wide-field photolysis of STX at 460 nm. In FIG. 2, the golden color disappears upon photolysis. But it takes long time, one-hour level, to treat MRSA by using a CW LED. CW LED also suffers from superficial treatment depth and significant heating issue, making this technology very changeling for clinical translation.

In order to bypass these hurdles, we propose using photons, a non-drug approach, to resensitize MRSA to conventional antibiotics. This approach only takes several minutes to resensitize these antibiotics and also it can save a broad spectrum of antibiotics. Particularly, we use pulsed laser to induce nano-scale pores and unanchor PBP2a proteins within MRSA membrane microdomains.

Firstly, a drug-free photonic approach to eliminating MRSA through effective photobleaching of STX, an indispensable anti-oxidative pigment residing inside the bacterium cell membrane (10-12) is disclosed herein. Initially we attempted to differentiate MRSA from non-resistant *S. aureus* (NRSA) by transient absorption imaging (see methods) of intrinsic chromophores. Intriguingly, once the cultured *S. aureus* was placed under microscope, the strong signal which was measured at zero delay between the 520-nm pump and 780-nm probe pulses, irreversibly attenuated over second time scale. This process was captured in real time (FIG. 1A).

Without being limited by any theory, we made hypothesis that a specific chromophore in *S. aureus* is prone to photobleaching under our transient absorption imaging setting. To verify the photobleaching phenomenon, we fitted the time-course curve (FIG. 1B) with a previously described photobleaching model (13):

$$y = y_0 + A * \frac{\exp\left(-\frac{t}{\tau_1}\right)}{1 + \frac{\tau_1}{\tau_2} * \left(1 - \exp\left(-\frac{t}{\tau_1}\right)\right)} \tag{1}$$

where t is the duration of light irradiation, y is the signal intensity, $y_0$ and A are constants, $\tau_1$ and $\tau_2$ are the bleaching constants for the first and second order bleaching, respectively. Derivation is detailed in supplementary text. First order bleaching happens at low concentration of chromophores (usually involved in singlet oxygen, $\tau_2=\infty$). Second order bleaching takes place when quenching within surrounding chromophores dominates ($\tau_1=\infty$). Strikingly, this photobleaching model fitted well the raw time-course curve ($R^2=0.99$) with $\tau_2=0.16$ s ($\tau_r=\infty$). Moreover, we found that oxygen depletion ($Na_2S_2O_4$: oxygen scavenger) has negligible effect on the bleaching speed since oxygen-depleted MRSA had a $\tau_2$ of 1.36±0.12 s and $\tau_2$ in control group was 1.00±0.20 s (FIG. 6A). The same phenomenon was observed in NRSA (FIG. 6B). Collectively, these data support a second order photobleaching process.

Next, we asked what chromophore inside *S. aureus* account for the observed photobleaching. It is known that carotenoids are photosensitive due to the conjugated C=C double bonds (14, 15). Therefore, we hypothesized that STX, a carotenoid pigment residing in the membrane of *S. aureus*, underwent photobleaching in our transient absorption study. To test this hypothesis, we treated MRSA with naftifine, a FDA-approved antifungal drug for STX depletion (11), the treated MRSA exhibited lower signal intensity (FIG. 1C) and slower photobleaching speed (FIG. 1D). FIG. ID shows that $\tau_2$ of naftifine-treated MRSA ($\tau_2$=0.39±0.07 s, $\tau_1$=∞) is 2.5 times longer than that of wild-type MRSA ($\tau_2$=0.16±0.01 s, $\tau_1$=∞). To further confirm the involvement of STX, we studied the CrtM mutant which is STX deficient (16) and observed no transient absorption signal (FIG. 1E). To avoid the systematic error aroused by single bacterium measurement, we investigated the clustered bacteria. It turned out that CrtM mutant cluster (FIGS. 1, G and H) only exhibited background induced by cross-phase modulation (17), whereas the wild-type MRSA cluster showed a sharp contrast against the background (FIG. 1F) and a fast photobleaching decay (FIG. 1H). Taken together, these data show that STX in *S. aureus* accounts for the observed photobleaching.

In our transient absorption study, when changing the 520-nm pump irradiance while fixing the probe intensity, both the photobleaching speed and transient absorption intensity altered drastically (FIGS. 7B and 8B), whereas the alteration of 780-nm probe irradiance only effected the transient absorption intensity but not the photobleaching speed (FIGS. 7A and 8A). Of note, β-carotene, which has a similar structure to STX, exhibits similar behavior such as laser irradiance dependence (FIGS. 9 A and B) and wavelength selection (FIGS. 9 C and D). These findings collectively imply a strong dependence of photobleaching efficacy on wavelength selection (fig. S4C), which is consistent with the fact that photobleaching is linked to the absorption of chromophore (18).

Figure 10:
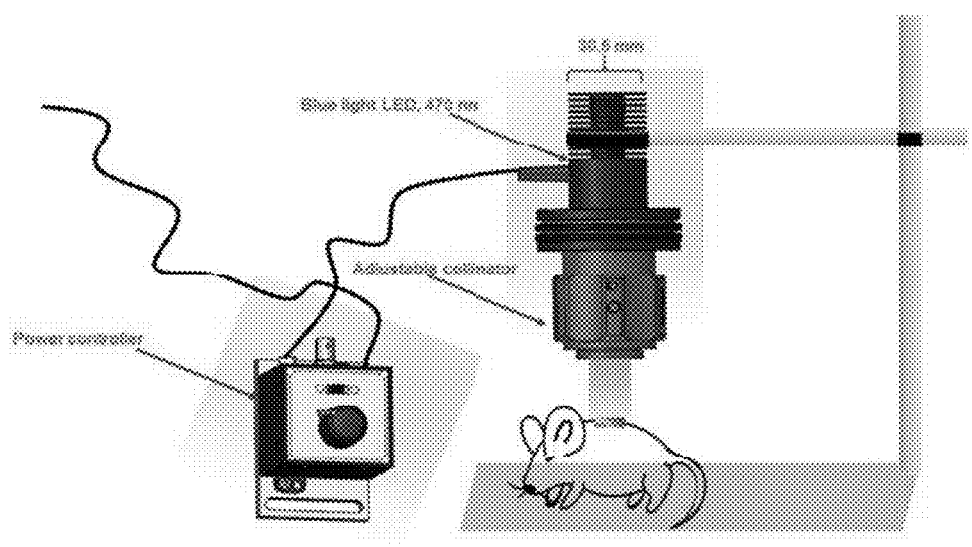
FIG. 10. Blue light LED apparatus.
Figure 11A:
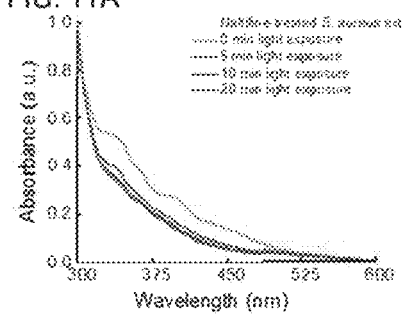
FIG. 11. Naftifine-treated *S. aureus* and CrtM mutant extract are immune to blue light exposure. Absorption spectrum of naftifine-treated *S. aureus* extract (FIG. 11A) and CrtM mutant extract (FIG. 11B) at different blue light exposure time.
(FIG. 11C). $OD_{470}$ from carotenoids of naftifine-treated *S. aureus* and CrtM mutant change towards blue light irradiance. High-performance liquid chromatography chromatographs of STX from naftifine-treated *S. aureus* (FIG. 11D) and CrtM mutant (FIG. 11E) at different blue light exposure time.
(FIG. 11F). Quantitative analysis of STX from naftifine-treated *S. aureus* and CrtM mutant during photobleaching process. Blue light, 470 nm, 90 mW (1 cm×1 cm) on the sample.
Figure 11B:
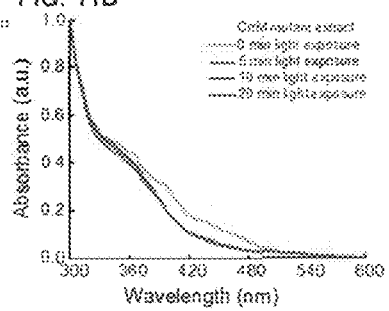
Figure 11C:
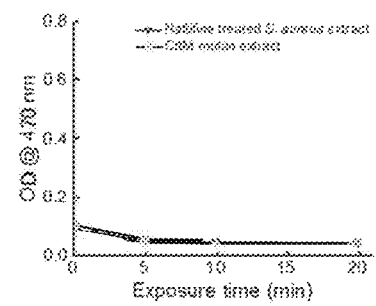
Figure 11D:
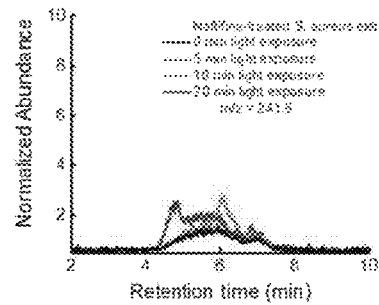
Figure 11E:
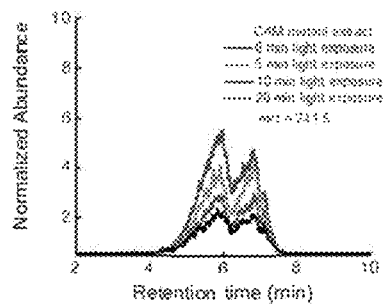
Figure 11F:
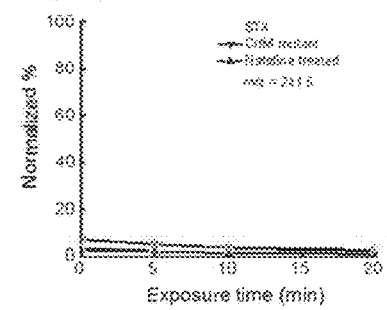
Figure 12:
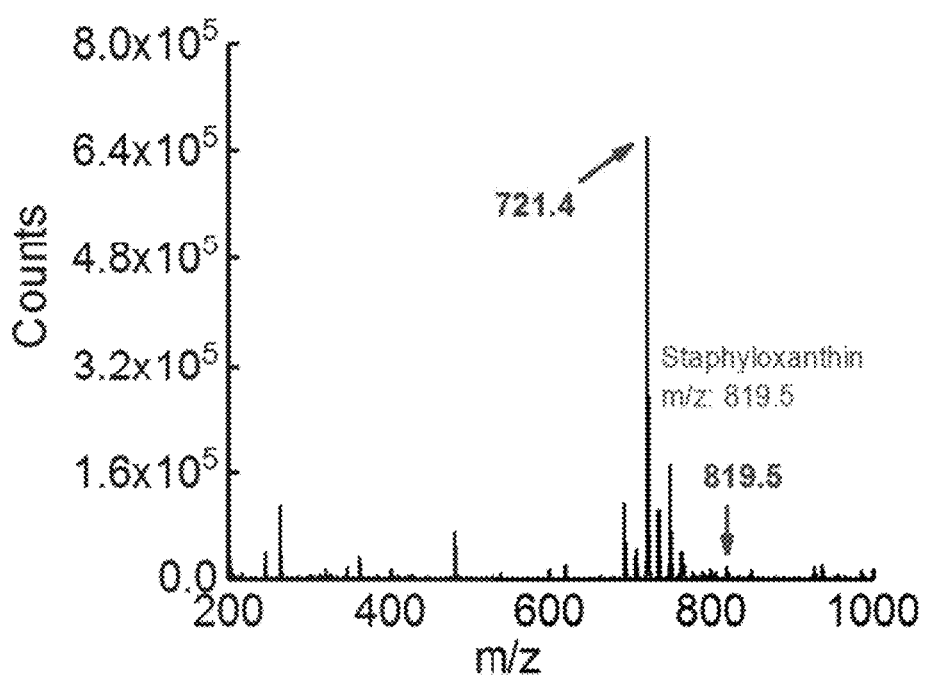
FIG. 12. The whole mass spectrum of STX.

To identify the optimal wavelength for bleaching STX, we measured the absorption spectrum of MRSA extract (FIG. 2A), which shows peaks around 450 nm. This result triggered us to build a portable blue light LED for wide-field bleaching of STX (FIG. 10). We exposed MRSA extract to blue light irradiance (90 mW) for different time lengths. It turned out that the distinctive golden color from *S. aureus* carotenoids disappeared within 30-min exposure (FIGS. 2, B and C), whereas group under ambient light remained unchanged (FIG. 2B). In addition, the decreasing absorption trace of *S. aureus* can be well fitted with equation (1) (FIG. 2D). We also found that extracts from naftifine-treated MRSA or CrtM mutant were immune to blue light exposure, indicated by no changes in the absorption spectra (FIGS. 11 A to C). These findings conclude that STX is prone to photobleaching under blue light irradiance.

To quantitate the photobleaching process, we exploited mass spectrometry to target STX during blue light irradiation. Figure. S8 exhibits the MS spectrum of *S. aureus* extract with m/z ranging from 200 to 1000 at a certain collision energy. An abundant peak appeared at m/z=721.4. Moreover, m/z=819.5 ([M+H*]) is consistent with the molecular weight of STX ($M_w$=818.5 g/mol). To find out the relationship between m/z=721.4 and m/z=819.5, we gradually increased the collision energy from 0 to 20 eV. As shown in FIG. 2(E), we found that m/z=721.4 is a product ion from m/z=819.5. These data proved that STX is the major species among the *S. aureus* extract. When the collision energy was higher than 20 eV, m/z=241.5, which comes from the precursor ion m/z=721.4, became dominant and presented a stable marker (FIG. 2E). Thus, to accurately quantify the amount of STX versus blue light dose, we targeted the HPLC area specifically from ion m/z=241.5 (retention time: 5.5 min, FIG. 2F). FIG. 2G depicts the blue light bleaching dynamics of STX. With 5-min (27 J/cm$^2$) exposure, only 10% of STX (from 3.29×10$^9$ bacteria) is left (FIG. 2G). A dose of 54 J/cm$^2$ attenuated all STX from ~10$^9$ bacteria. As a control, naftifine-treated and CrtM mutant *S. aureus* extract had negligible response to blue light exposure (FIGS. 11 D to F).

Next, we employed TOF-MS/MS (see methods) to elucidate how STX is decomposed during the photobleaching process. Different from the m/z=819.5 in HPLC-MS/MS, STX showed a peak at m/z=841.5 (FIG. 2H), which is an adjunct between STX and Na$^+$ (Retention time: 9.5 min). Degradation of STX would definitely bolster the aggregation of some chemical segments. Through screening, we found a patch of the products existing after STX photobleaching (data not shown here). Notably, a significantly intensity-increased peak at m/z=643.4 (FIG. 2I), which is the adjunct between part of the STX along with H$^+$. FIG. 2J illustrates the breakdown of conjugated C=C bonds of STX during blue light-activated photobleaching process.

Figure 3A:
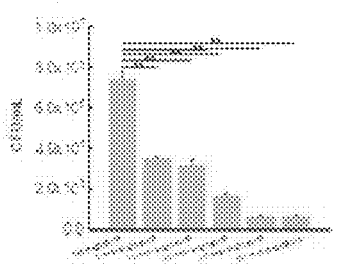
(FIG. 3A). The effect of blue light dose upon the survival percent of wild-type MRSA. Blue light: 460 nm, 60 mW/cm$^2$. N=3.
Figure 3B:
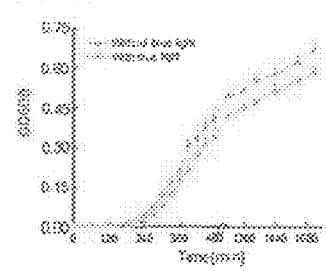
(FIG. 3B). Growth curve of untreated group and blue light-treated group. Blue light: 460 nm, 120 J/cm$^2$.
Figure 13A:
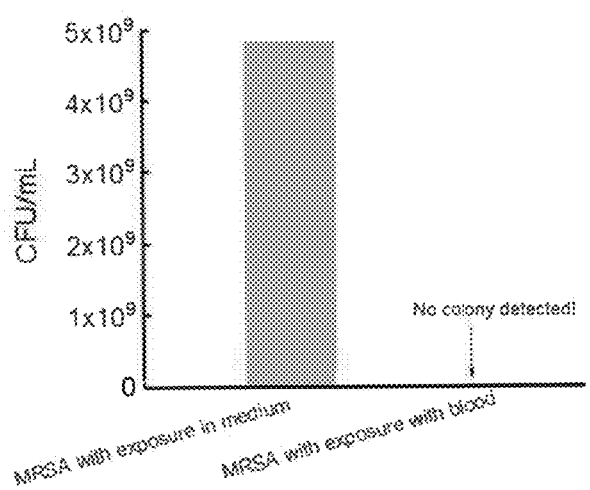
FIG. 13. Human whole blood effectively scavenges MRSA (FIG. 13A) and NRSA (FIG. 13B) after photobleaching by pump probe microscopy. Blue light: 440 nm, 10 mW, 1 h light exposure time. Then for the control group, after exposure we culture them in the medium for 9 h. For the experimental group, bacteria were cultured in the fresh whole blood for 9 h.
Figure 13B:
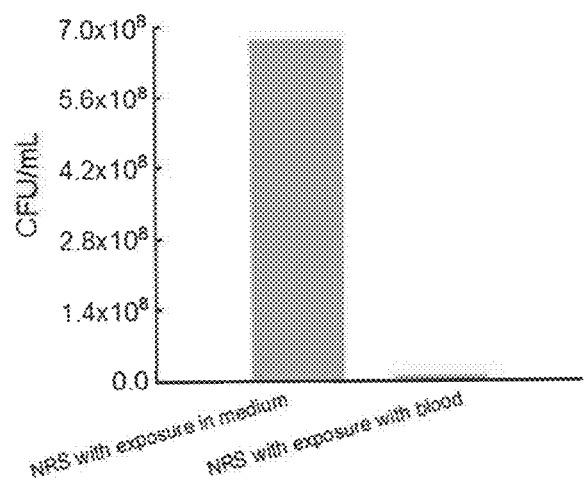
Figure 14:
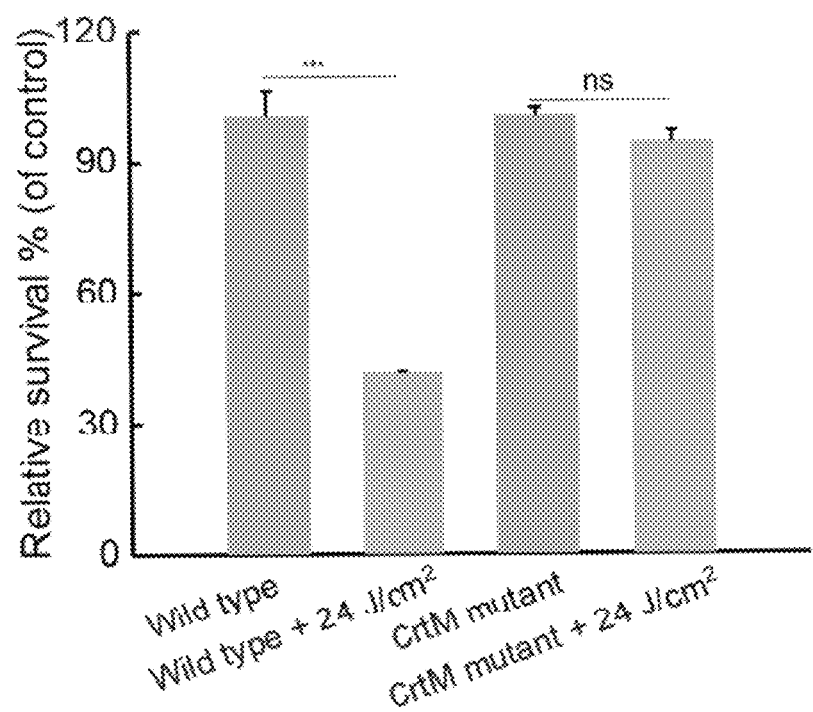
FIG. 14. Staphyloxanthin sensitizes *S. aureus* towards blue light-based killing.

Since STX is critical to the integrity of *S. aureus* cell membrane (16), we asked whether blue light could eradiate MRSA through bleaching STX. It was found that increasing blue light dose could kill a growing number of MRSA (FIG. 3A), in consistence with blue-light-based bacterial killing (19, 20). Moreover, we show that wild type MRSA is more sensitive to blue-light than the CrtM mutant (FIG. 13). Nevertheless, the dependence of antimicrobial effect upon blue light dose became opaque when blue light dose is higher than 216 J/cm$^2$. To investigate this reason, we carried out a real-time measurement of bacterial growth after blue light exposure. It turned out that after 10-min blue light exposure, MRSA recovered after being cultured in the medium for 30 min (FIG. 3B). Therefore, photobleaching STX alone is not sufficient to kill MRSA completely.

Figure 3C:
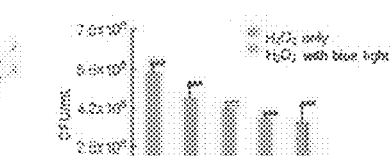
(FIG. 3C). CFUs result of $H_2O_2$ only-treated group and blue light plus $H_2O_2$-treated group at different $H_2O_2$ concentrations. Blue light: 60 mW, 108 J/cm$^2$. $H_2O_2$ incubation time: 20 min.
Figure 3D:
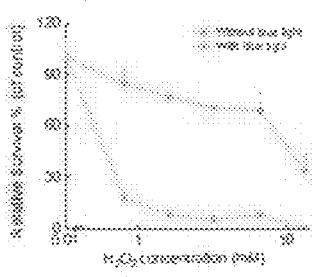
(FIG. 3D). CFUs result of $H_2O_2$ only-treated group and blue light plus $H_2O_2$-treated group. $H_2O_2$: 13.2 mM (0.045%), 20-min culture time.
Figure 3E:
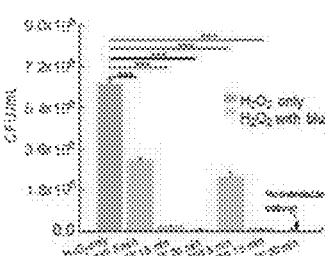
(FIG. 3E). Survival percent of MRSA from blue light only-treated group and blue light plus $H_2O_2$-treated group at different $H_2O_2$ concentrations. Blue light: 470 nm, 108 J/cm$^2$.
Figure 3F:
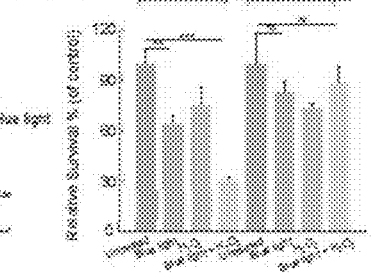
(FIG. 3F). Blue light sensitizes MRSA to $H_2O_2$ killing compared to *S. epidermidis*. Blue light: 470 nm, 60 J/cm$^2$. $H_2O_2$:13.2 mM, 5-min culture time.

Because STX also serves as an indispensable antioxidant for MRSA, we then asked whether photobleaching of STX could sensitize MRSA to reactive oxygen species (ROS). We compared the survival percent of wild type MRSA after $H_2O_2$ treatment with or without blue light exposure. When MRSA was treated subsequently with an increasing concentration of $H_2O_2$ after blue light irradiance (108 J/cm$^2$), significant reduction (p<0.001) was obtained (FIG. 3C). 13.2 mM of $H_2O_2$ combined with blue light exposure (108 J/cm$^2$) eradicated all MRSA (~10$^7$, FIG. 3D). To dig out whether $H_2O_2$ and blue light work together as synergistically or additively, we changed the blue light dose while fixed the concentration of $H_2O_2$(FIG. 3E). Combined those two effects together, a distinctive synergistic effect was found by using an established protocol (see methods). Noteworthy, this treatment does not harm benign species such as *S. epidermidis* (FIG. 3F) due to the lack of STX in the benign species.

Figure 3G:
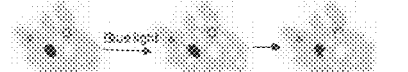
(FIG. 3G). Schematic cartoon illustrates how blue light assists ROS inside the macrophage cells to kill intracellular MRSA (not drawn to scale). Yellow dots: MRSA 400. Gray dots: MRSA 400 after blue light exposure.
Figure 3H:
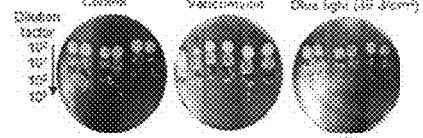
(FIG. 3H). CFUs results (n=3-6) of MRSA 400-infected macrophage cells from control (untreated), vancomycin-treated and blue light-treated groups.
Figure 3I:
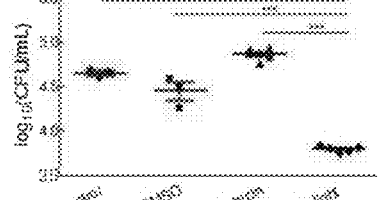
(FIG. 3I). Statistical analysis of the CFUs results from different groups.

Studies dating back to at least 50 years have demonstrated that MRSA is able to invade and survive inside the mammalian cells, especially, the phagocytic cells which can't scavenge all the intracellular MRSA (21). Current antibiotics failed to clear the intracellular MRSA because of the difficulty in delivering drugs through the phagocytic membrane. Incomplete clearance of MRSA poses an alarming threat to the host mammalian cells (21). Since we have proved that blue light and $H_2O_2$ synergistically kill MRSA, we wondered whether blue light could synergize with intracellular ROS to eliminate MRSA inside the macrophages (FIG. 3G). We first infected the macrophage cells by incubation with MRSA 400 for 1 h. Then we applied 48 $J/cm^2$ of blue light to irradiate the macrophage cells for 2 min per each dose, two doses in total with 6-h interval between the two doses. Colony formation units (CFUs) counting was conducted (FIG. 3H). FIG. 3I compiled the statistical analysis of different groups. Noticeably, about 1-log reduction was found in the blue light-treated group in comparison with the untreated group. On the contrary, vancomycin showed no effect in killing intracellular MRSA 400. Additionally, we found that whole blood could eradicate most of MRSA after STX bleaching by blue light (FIG. 15, A and B). These findings collectively suggest that blue light could assist neutrophils to scavenge S. aureus.

Biofilms are highly resistant to antibiotics due to their failure to penetrate the matrix of biofilm termed extracellular polymeric substances. Compared to antibiotics treatment, an unparalleled advantage of our photobleaching therapy lies in that photons can readily penetrate through a cell membrane or biofilm. To explore whether STX bleaching could eradicate MRSA inside a biofilm, we grew biofilms on the bottom of glass dish and then applied treatment on the biofilms. Blue light alone killed 80% MRSA. Blue light plus low-concentration $H_2O_2$ killed 92% MRSA. In contrast, application of vancomycin only killed 70% MRSA (FIGS. 15 A and B). These results suggest new opportunities of eradicating sessile bacterial cells inside biofilm that often withstand antibiotics (22).

Figure 16A:
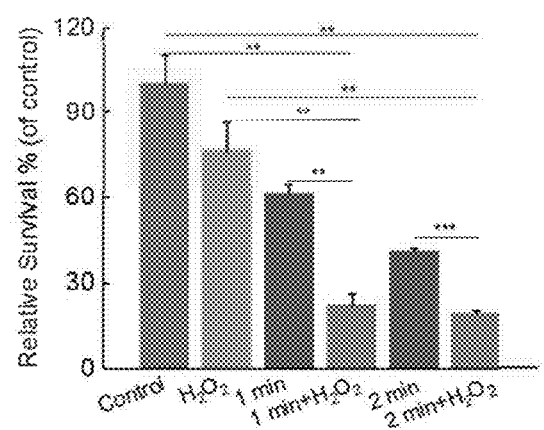
FIG. 16. Survival percent of MRSA depends on blue light dose (FIG. 16A) and $H_2O_2$ culture time (FIG. 16B). Blue light: 1-2 min (12-24 J/cm$^2$). $H_2O_2$: 13.2 mM.
(FIG. 16B). Fix the $H_2O_2$ culture time (20 min). Fix the blue light irradiance (24 J/cm$^2$).
Figure 16B:
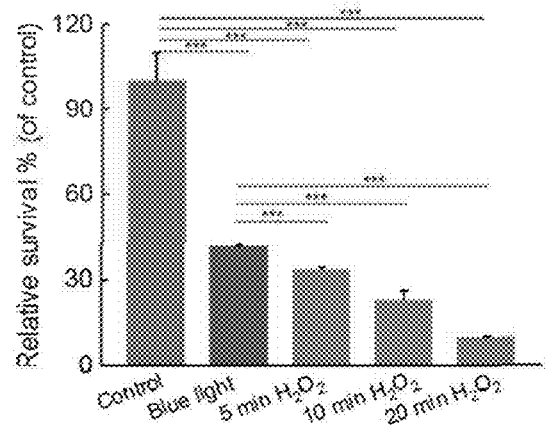

Skin infections such as diabetic foot ulceration and surgical site infections (23) are a common cause of morbidity in the hospital and community. Notably, S. aureus accounts for 40% of skin infectious (24). Thus, we carried out a preclinical study to explore the potential of STX bleaching for treatment for S. aureus-induced wound infections. To facilitate the operation of in vivo experiment, we first proved that 2-min blue light exposure (24 $J/cm^2$) could cause significant reduction of survival percent of MRSA (FIG. 16A). Two times antimicrobial efficiency was obtained when cultured with $H_2O_2$ (20 min, 13.2 mM) subsequently. Furthermore, 5-min culture time with $H_2O_2$ after 2-min blue light exposure (24 $J/cm^2$) effectively scavenged MRSA by 60% (FIG. 16B).

Figure 4A:
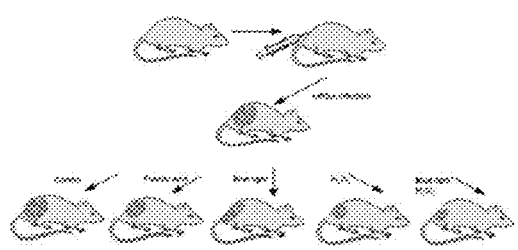
(FIG. 4A). Schematic cartoon demonstrates the animal experimental process (not drawn to scale).
Figure 4B:
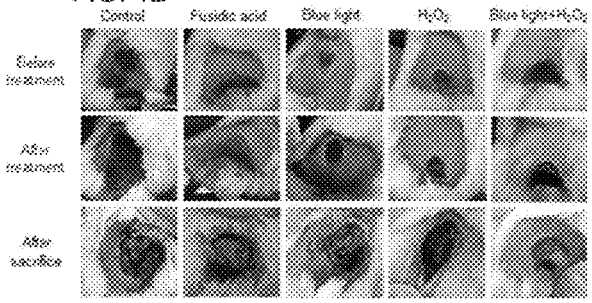
(FIG. 4B). Physiological wounds condition of four different groups before, after treatment and after sacrifice. Red arrow: pus formation.

To induce MRSA-infected wound (FIG. 4A), we applied $10^8$ (in phosphate buffered solution (PBS)) of MRSA 300 to severely irritate mice skin (N=5 per group, five groups). Sixty hours post infection, an open wound formed at the site of infection (FIG. 4B (top)). Corresponding treatment was applied to each group (FIG. 4A), twice a day for three days. All treated groups demonstrated the symptom of healing, whereas the untreated group suffered from heavy infection (FIG. 4B (middle)). After sacrifice of those mice, we examined the physiological condition of the wounds. It turned out that the untreated, fusidic acid-treated and blue light-treated groups all showed the formation of pus aroused from inflammatory response of mice, whereas the $H_2O_2$-treated group along with blue light plus $H_2O_2$ treated group didn't show this sign (FIG. 4B (below)).

Figure 4C:
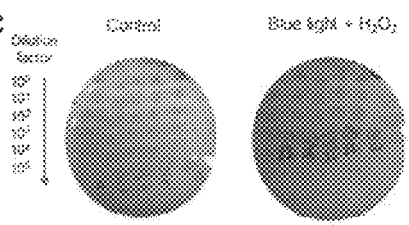
(FIG. 4C). CFUs plates of the untreated group and the blue light plus $H_2O_2$-treated group.
Figure 4D:
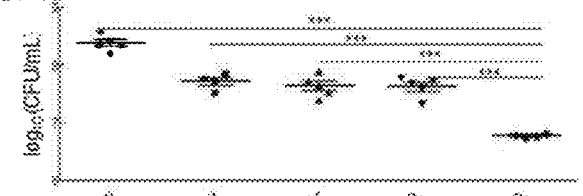
(FIG. 4D). Statistical analysis of the CFUs results from five different groups. N=4-5.

To quantify the antimicrobial effectiveness, we counted the number of bacteria survived inside the wound tissue by conducting CFUs study. Wound tissues were harvested into 2-mL PBS, homogenized, and then inoculated serial diluted solution onto mannitol salt agar plate (MRSA specific). The CFUs results demonstrated that blue light and $H_2O_2$ treated group had around 1.5-log reduction compared to the control group (FIG. 4C). Statistical analysis of CFUs from blue light and $H_2O_2$-treated groups depicted significant MRSA reduction compared to other groups (FIG. 4D). Noteworthy, blue light and $H_2O_2$-treated group has around one more log reduction than fusidic acid-treated group (FIG. 4D).

Figure 4E:
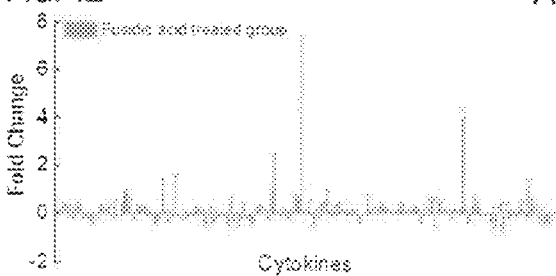
(FIG. 4E-F). In comparison with untreated group, the fold change from 200 kinds of cytokines in fusidic acid-treated group (FIG. 4E), blue light plus $H_2O_2$-treated group (FIG. 4F).
Figure 4F:
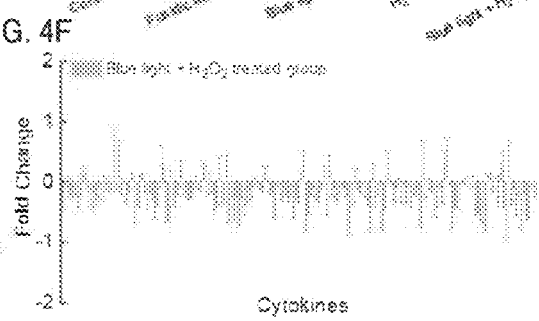
Figure 17A:
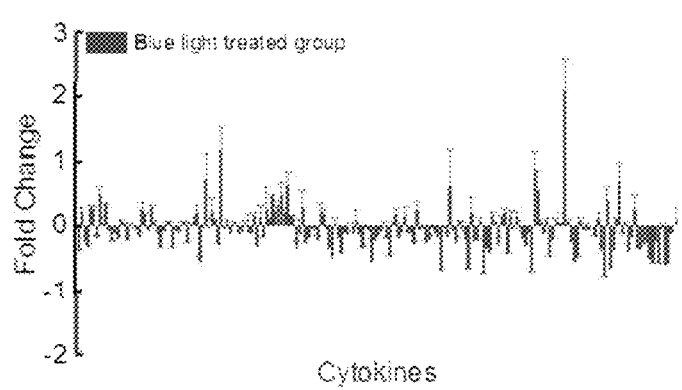
FIG. 17. Cytokine data analysis for blue light-treated group (FIG. 17A) along with $H_2O_2$-treated group (FIG. 17B).
Figure 17B:
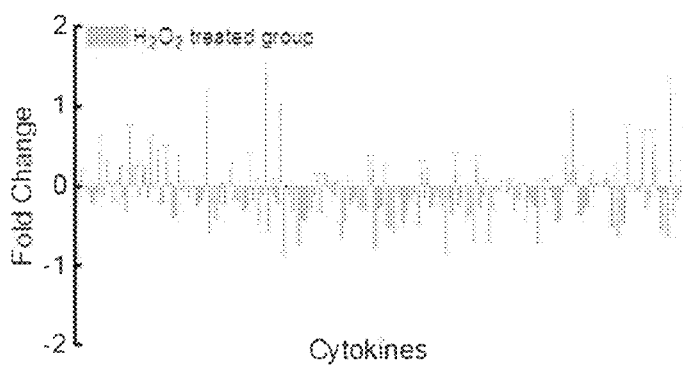
Figure 18B:
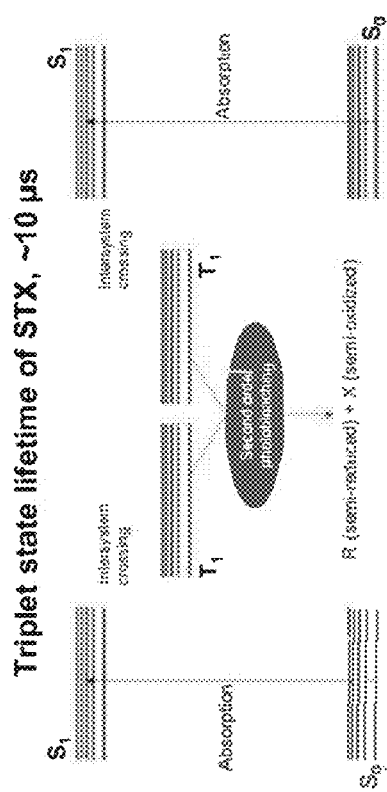
(FIG. 18B) Photolysis process follows a bi-molecule behavior due to triplet-triplet annihilation. This process highly depends on the molecule concentration. T* lifetime of STX is around 10 us. Using high-intensity nanosecond pulsed laser (with pulse width less than T* lifetime) to transiently populate STX molecules to their T* state, due to their high concentration within MRSA membrane microdomains, we can dramatically increase the photolysis efficiency and speed. Nanosecond pulsed laser can also dramatically improve photolysis depth due to its high laser fluence and nonlinear nature of STX photolysis. Meanwhile we can also solve the heating issue for CW LED.
Figure 18A:
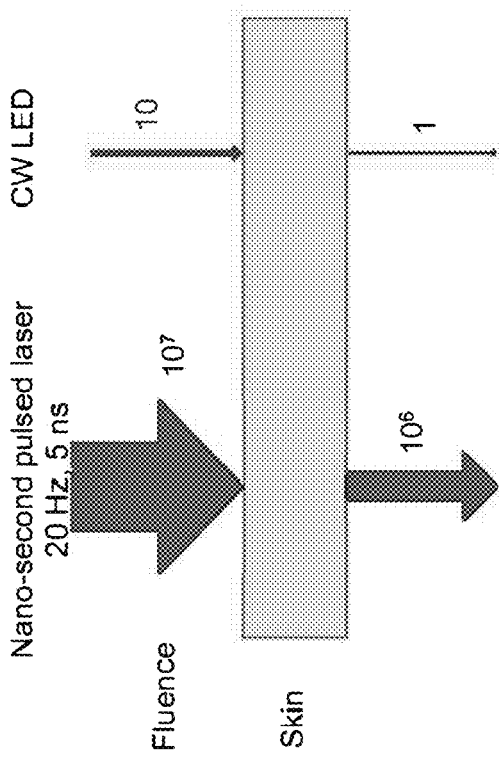
(FIG. 18A) Nanosecond pulsed laser fluence shows roughly 6 orders of magnitude larger than CW LED on surface (with power of 120 mW, repetition rate of 20 Hz, wavelength of 460 nm, beam size of 10 mm, pulse width of ~5 ns for nanosecond pulsed laser; with power of 120 mW, central wavelength of 460 nm, beam size of 10 mm for CW LED).
Figure 21:
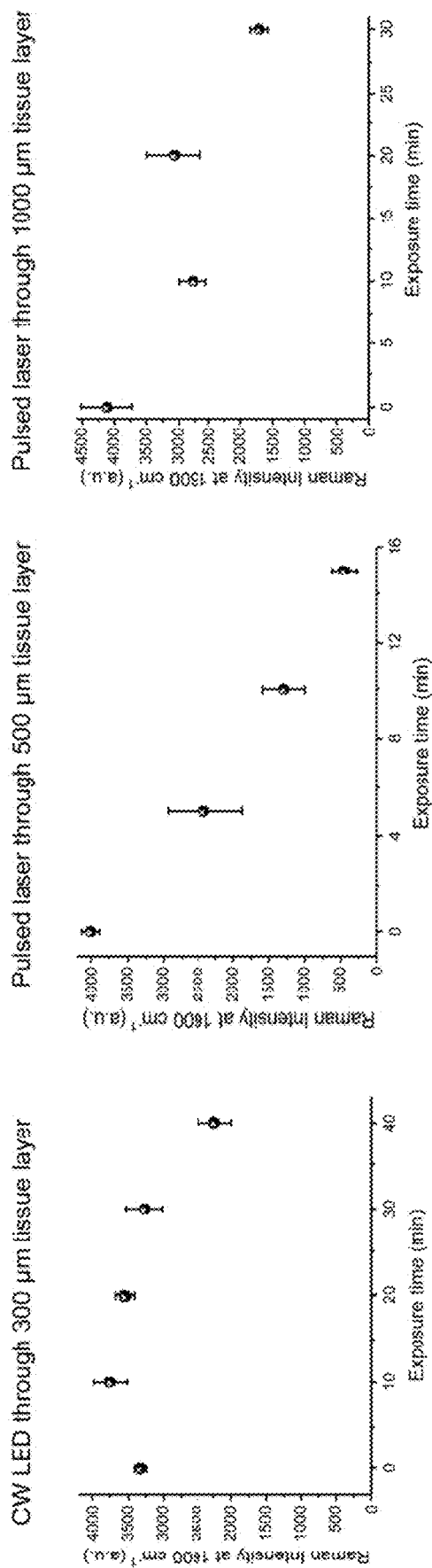
Figure 22:
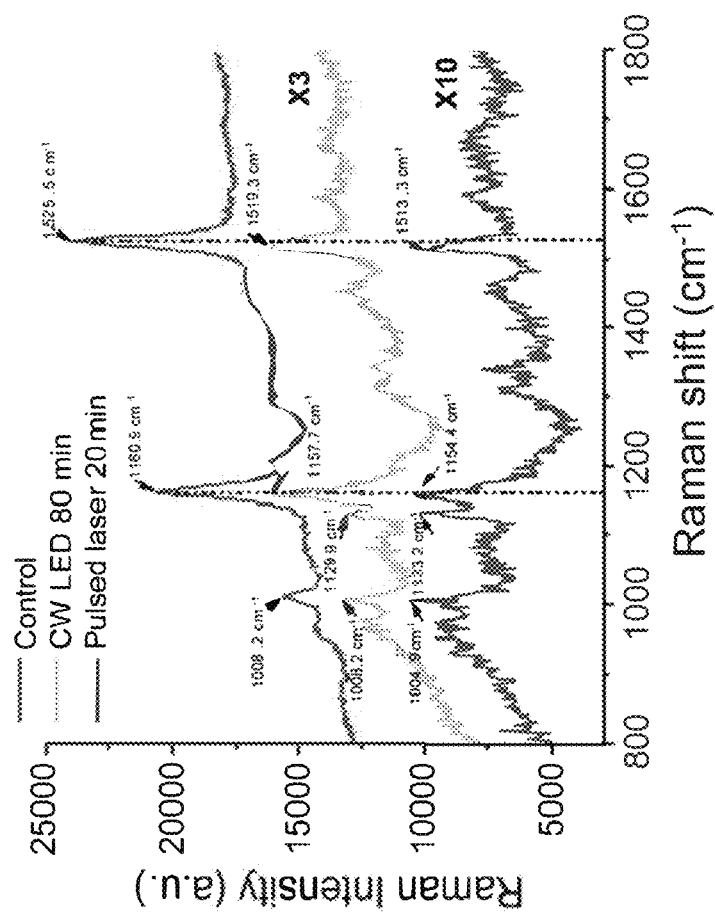

To quantify the physiological condition of the wound tissues, we measured the concentrations of 200 kinds of cytokines (Table. 1) from the supernatant of homogenized tissue solution. Cytokines are small secreted proteins released by cells and have specific effect on the interactions and communications between cells (25). Over 85% of these 200 cytokines from blue light and $H_2O_2$-treated group (FIG. 4F) have negative fold change, whereas around 50% of cytokines from fusidic-treated group have negative fold change (FIG. 4(E)). Moreover, compared with cytokine fold change from blue light-treated group (FIG. 17A) along with $H_2O_2$-treated group (FIG. 17(B)), blue light and $H_2O_2$-treated group exhibited the highest percent of negative fold change among those cytokines, indicating the lowest inflammatory response from wound tissue. This result solidified the synergy between blue light and $H_2O_2$ in treating MRSA-caused wound infections. Taken together, our findings show the exciting potential of treating drug-resistant bacteria by exploring the unique photochemistry of pigments inside the bacteria.

Figure 27A:
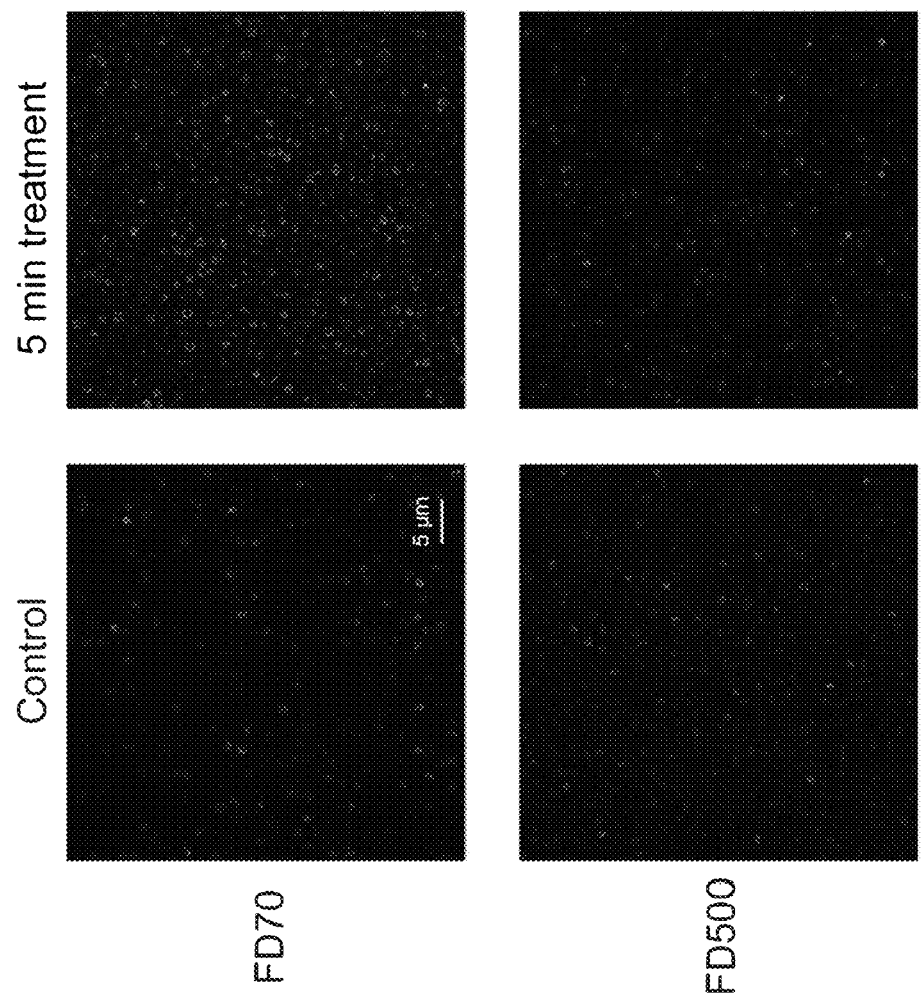
Figures 27, 27B:
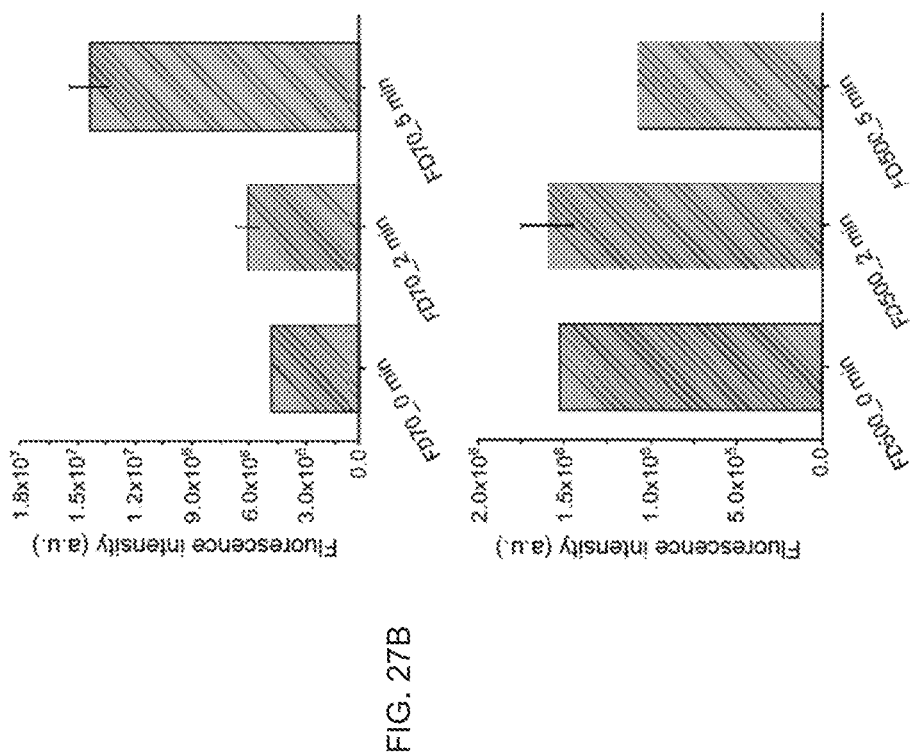
Figure 30:
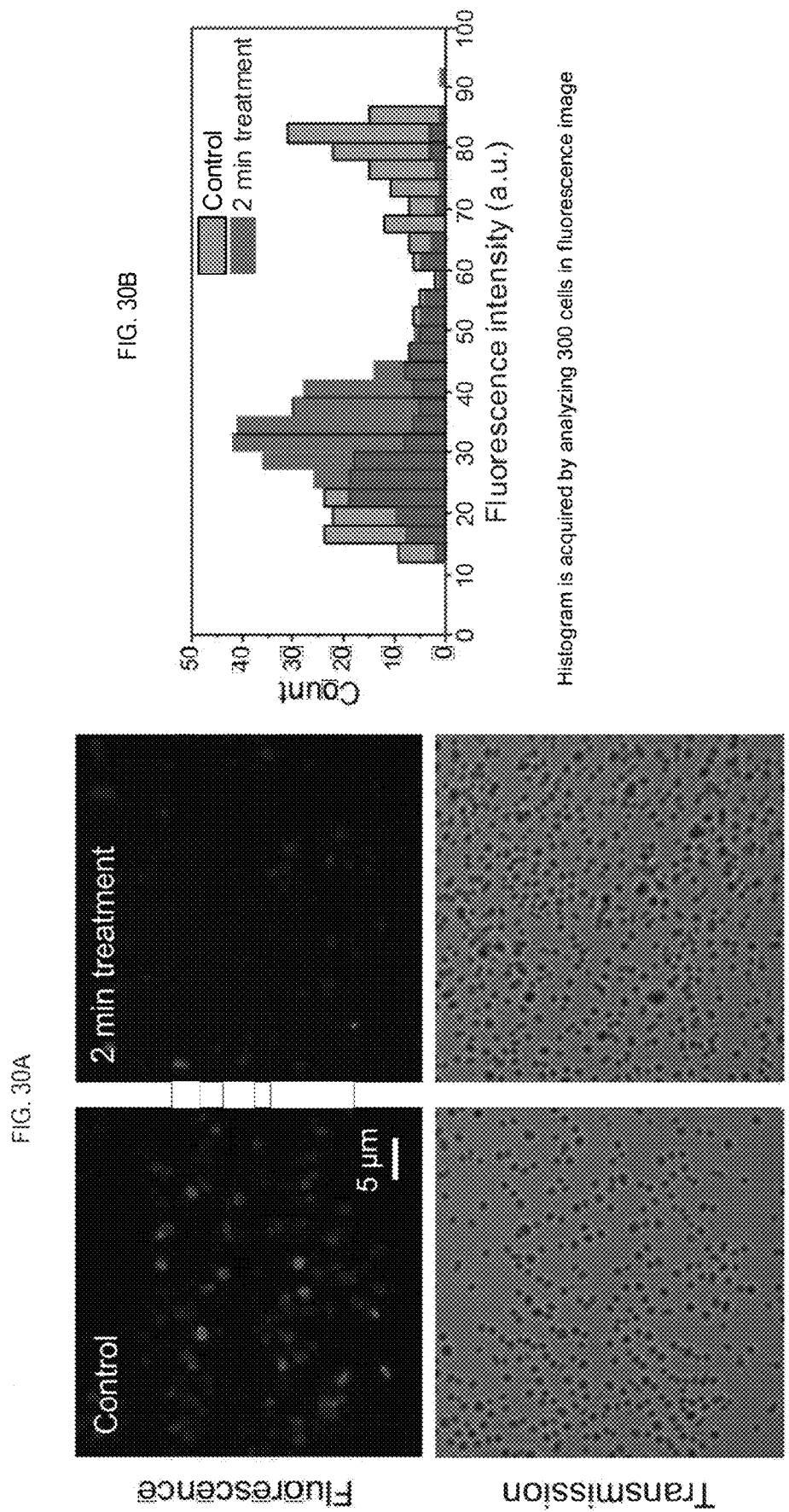
FIG. 30. PBP2a is unanchored from membrane microdomains via photolysis of STX.

In this disclosure we have shown that high-intensity pulsed laser enable dramatically faster and deeper photolysis of STX. See FIG. 20 and its legend. The pulsed laser dis-assembles MRSA membrane microdomains by creating membrane pores (see FIG. 27A, B and their legend) and unanchoring PBP2a proteins (See FIG. 30 and its legend). This photonic approach can be developed as a therapeutic platform to revive a broad spectrum of conventional antibiotics, as exemplified in FIG. 32 and its legends.

Without being confined to any theory, it is hypothesized that increased cell membrane permeability is induced by STX photolysis. This is proved by SYTOX Green study exemplified in FIGS. 23 and 24 (See their legends).

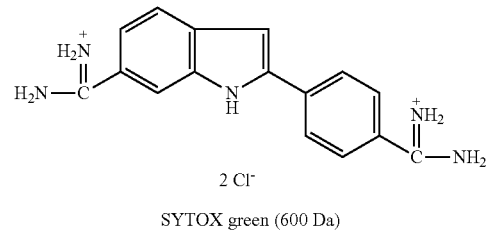 [SMILES: N=C(N)c1ccc(-c2cc3ccc(C(=N)N)cc3[nH]2)cc1]

SYTOX green (600 Da)

Figure 25:
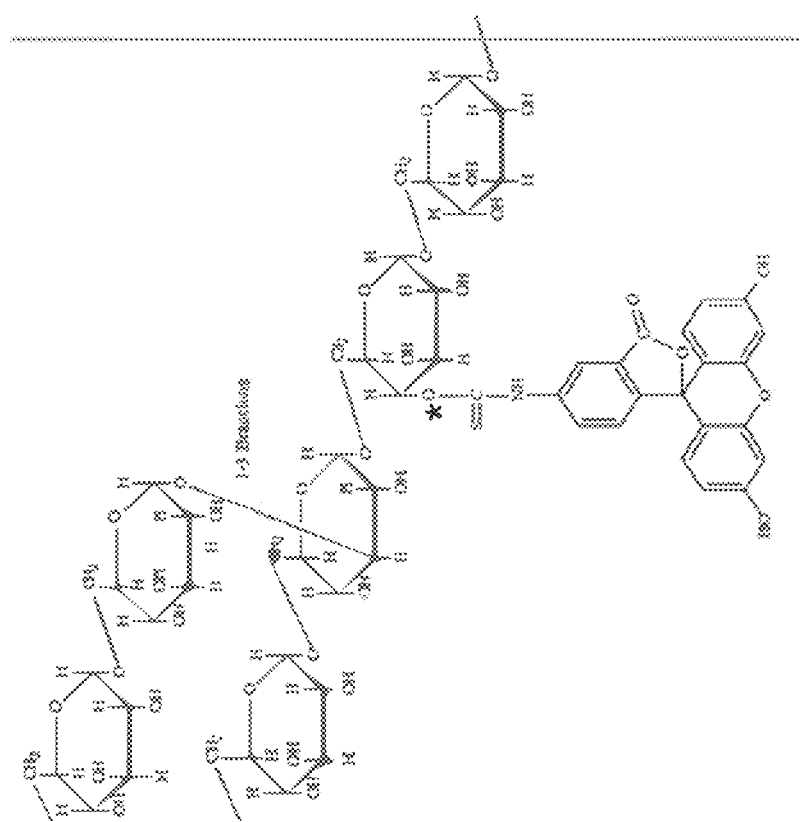
Figure 26:
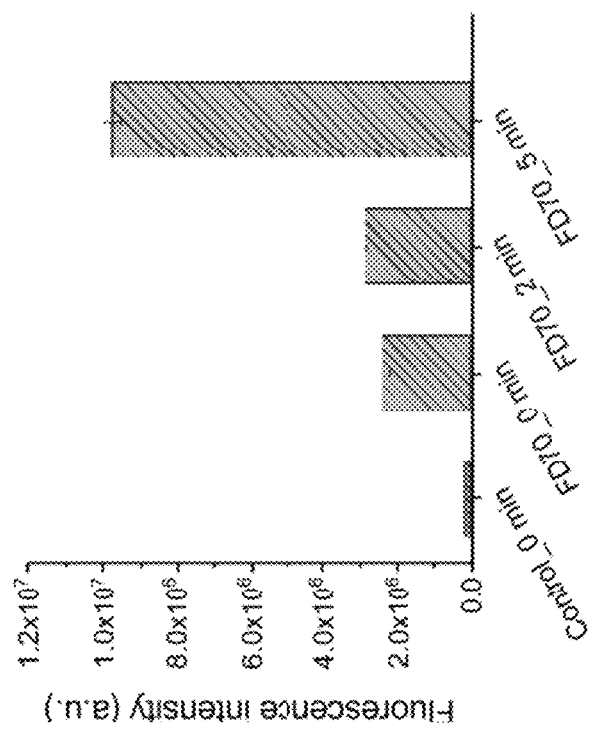
Figure 28:
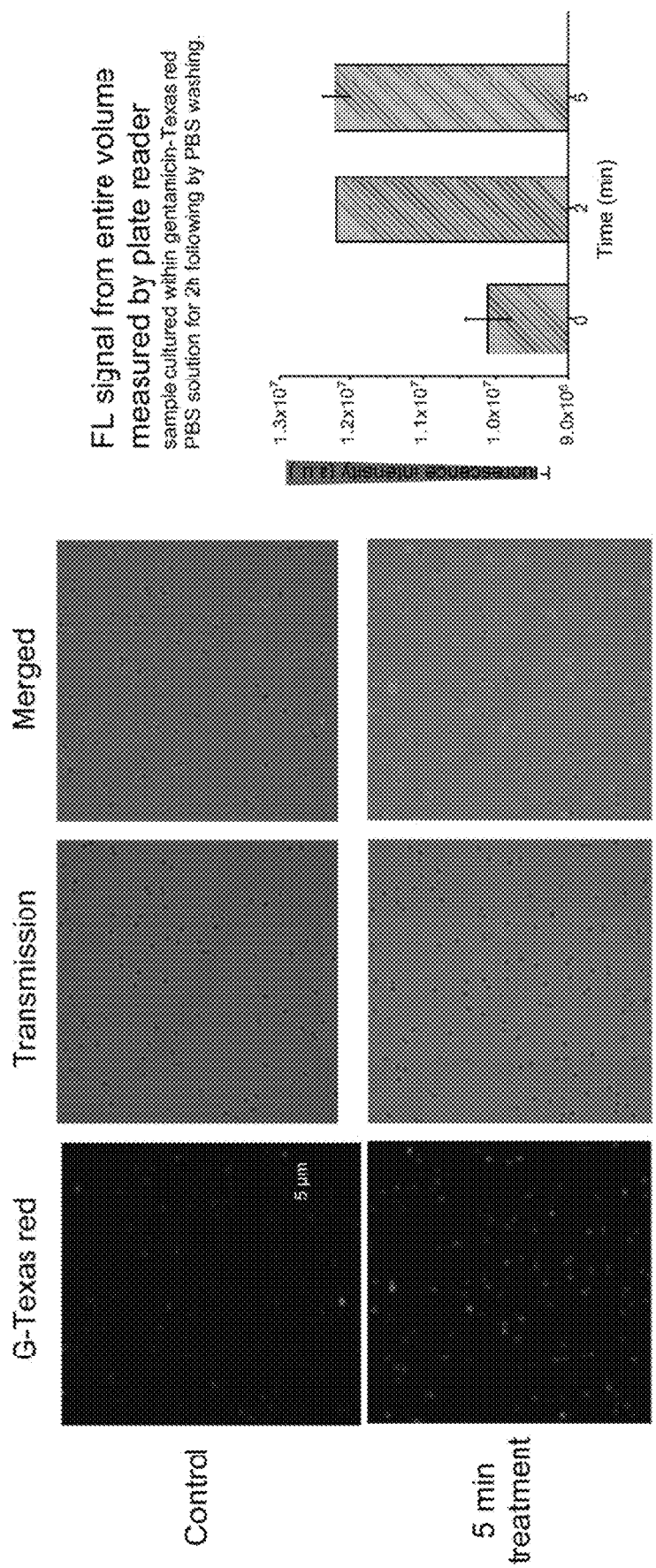

Further quantification of membrane pore size was studied by FITC-Dextran. Photolysis of STX created membrane poration with pores size up to ~10 nm level. These pores enable intracellular delivery of antibiotics targeting intracellular activities. See FIGS. 25, 26, 28 and their legends.

Figure 29:
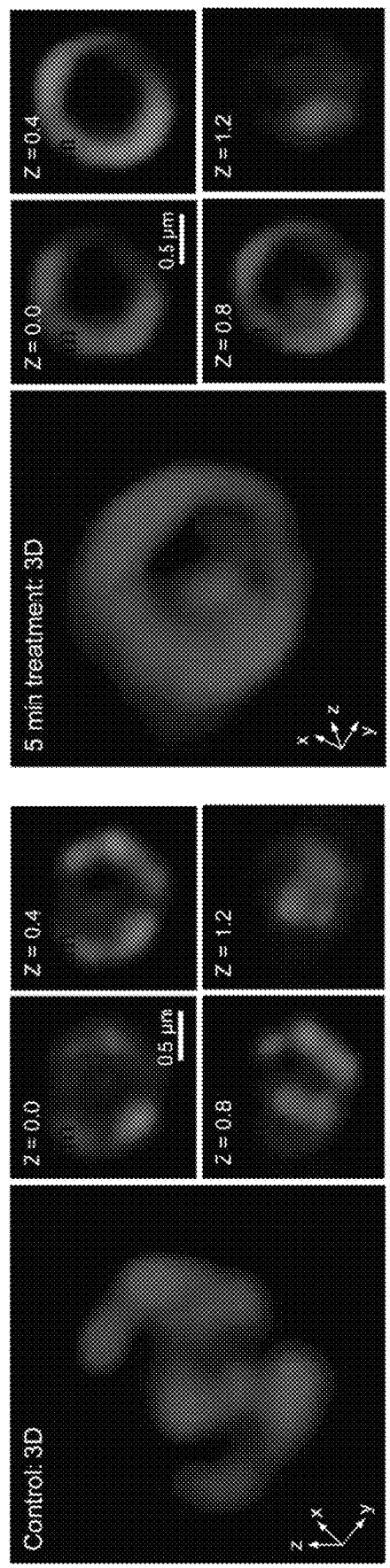
FIG. 29. PBP2a accumulation within membrane microdomains and its change induced by laser treatment. Immunostaining of PBP2a on MRSA cell membrane is performed by using rabbit anti-PBP2a as the primary antibody and Cy5 as the secondary antibody. Structured illumination microscopy herein is applied to image PBP2a amount and distribution with a lateral resolution about ~130 nm and axial resolution of ~150 nm. Based on the imaging results, PBP2as are not uniformly distributed on cell membrane; rather they are highly concentrated within the membrane microdomains. The images are acquired from two representative cells, one from control group and the other one from 5 min treated group, respectively. The MRSA cell from control group shows roughly 7 functional membrane microdomains. But after 5 min treatment, a significant drop is seen in its signal intensity (verified by confocal laser scanning microscope in the FIG. 30). Compared with control group, PBP2a proteins in 5 min treated group have the trend to disperse to surrounding membrane areas, which significantly reduce the signal contrast between functional membrane microdomains and its surrounding areas.

Without being limited by any theory, it is also believed that photolysis of STX disassembles functional membrane microdomains by unanchoring PBP2a proteins from membrane microdomains. Structured illumination microscopy in FIG. 29 and its legends demonstrated PBP2a accumulation within membrane microdomains and its change induced by laser treatment.

Figure 31B:
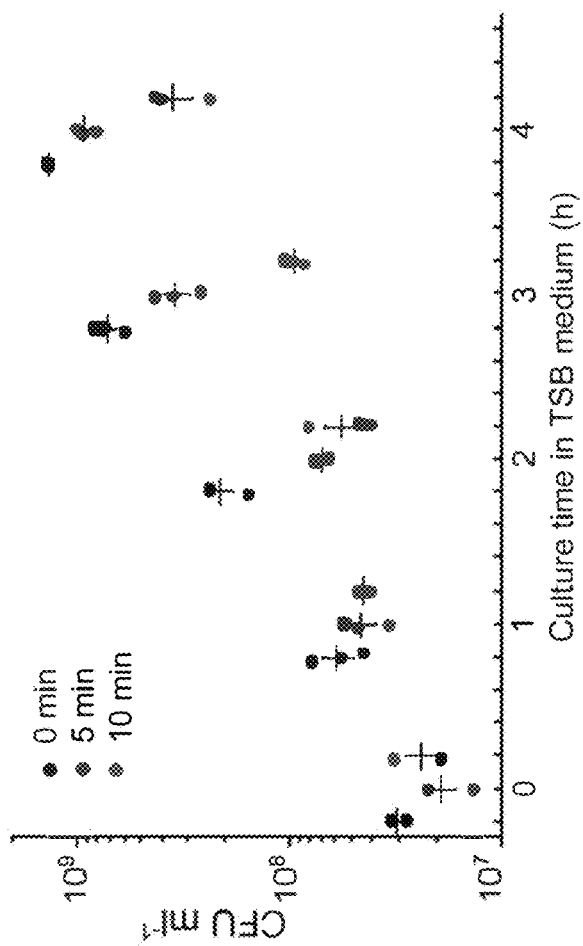
(FIG. 31B) CFU results of MRSA cells treated by pulsed laser with different culturing time in TSB medium. From these results, immediate CFU counting showed MRSA are just dramatized by laser, not immediately killed. When MRSA are cultured in PBS without nutrition, the longer treatment time, the more MRSA cells are killed, indicating that dramatized MRSA dies without nutritious medium. But 2-log reduction by laser treatment alone is not complete. Remarkably, when MRSA cells were cultured after laser treatment in nutritious medium, most of the MRSA cells are able to recover. Quantification of recover time is determined by culturing them in nutritious medium with different time and then followed by CFU counting. Comparing recovery curves of untreated, 5 min treated, 10 min treated groups show recovery time dependent on laser treatment time. MRSA cells need 0.5-1 h to recover after 5 min laser treatment and 1-2 h after 10 min laser treatment.
Figure 31A:
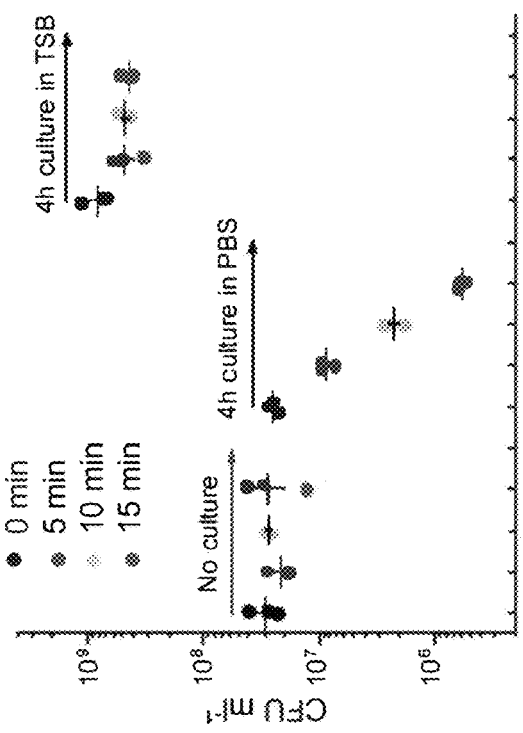
(FIG. 31A) CFU results of MRSA cells treated by pulsed laser without culturing, with 4-hour culturing in PBS, and 4-hour culturing in TSB medium.

Furthermore, photo-disassembly of functional membrane microdomains also revives a broad spectrum of antibiotics against MRSA. We have shown that MRSA with compromised membrane after laser treatment is able to recover if they are put in a nutritious medium. However, significant portion of MRSA with damaged cell membrane dies if without nutritious medium. See FIG. 31 and its legend. It is worth noting that the survival percentage and recovery time of laser treated MRSA depends on laser treatment time. MRSA cells need 0.5-1 hour to recover after 5 min laser treatment and 1-2 hour after 10 min laser treatment. Light treatment alone (even for a pulsed laser) is not sufficient for complete MRSA eradication. This suggests that seeking synergy with conventional antibiotics or new antibiotic drugs is a new direction of treating superbugs.

Figure 32:
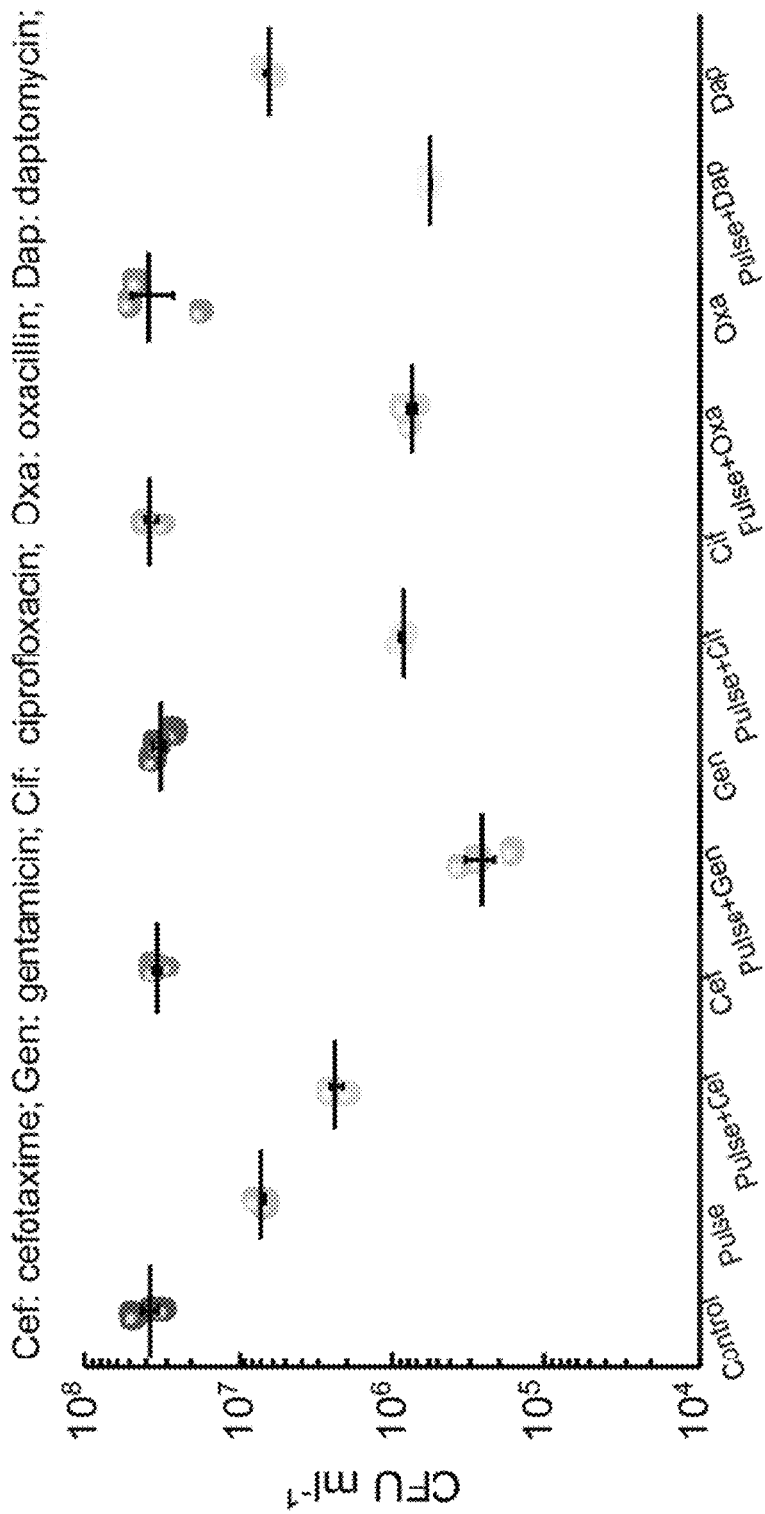
FIG. 32. Synergy between laser treatment and conventional antibiotics in killing MRSA. Laser treatment induces large membrane pores and removes significant amount of PBP2a from cell membrane. It created a great opportunity to find synergy with some conventional antibiotics, thus to revive these conventional antibiotics. The figure here shows the CFU results of stationary-phase MRSA cells in control group, 5 min laser-treated group, antibiotics-treated groups, and 5 min laser plus antibiotics-treated groups. The concentration of antibiotics applied here is 10 MIC for all these antibiotics. Compared with the control, 5 min laser treatment alone kills MRSA by less than one log. No obvious killing is observed for all tested antibiotics except for daptomycin, the last resort antibiotics for MRSA. But when combined laser treatment with antibiotics, very obvious synergy for nearly every class of antibiotics shown here is observed. These antibiotics include cefotaxime, gentamicin, ciprofloxacin, and oxacillin. Gentamicin has show more than 2 log reduction compared with control group.

The synergy between photo-disassembly of membrane microdomains and conventional antibiotics is proved in FIG. 32. Nearly every class of antibiotics we showed demonstrated synergy against MRSA. These include cefotaxime, gentamicin, ciprofloxacin, oxacillin, and daptomycin. Gentamicin has shown more than 2 log reduction of stationary-phase MRSA when combined with pulsed laser treatment.

Figure 33:
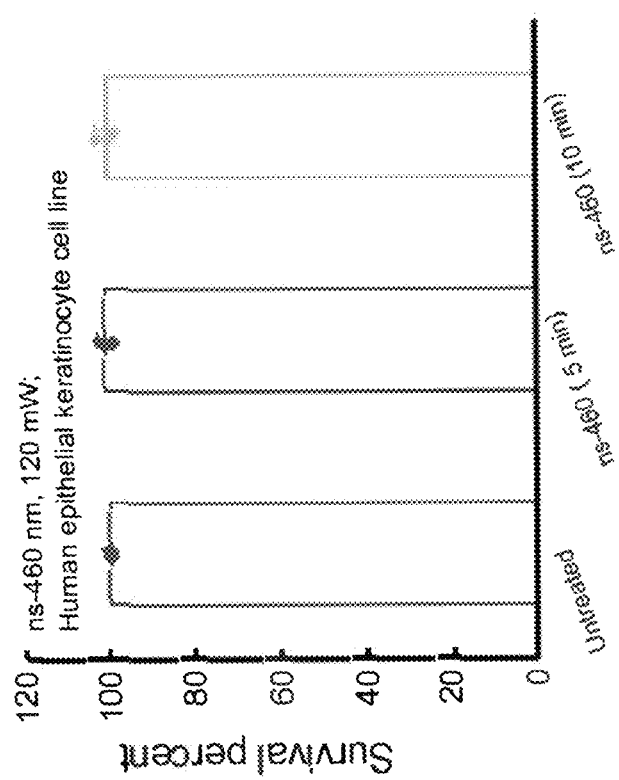
FIG. 33. Photo-toxicity of laser treatment on human cells. Survival percent of human epithelial keratinocyte cell line was monitored for untreated group, 5 min and 10 min treated groups for 460 nm nanosecond pulsed laser. No phototoxicity has been detected with illumination time up to 10 mins. With volunteer's arm illuminated by the same laser beam, no heating is reported and no any observable photo-damage found. The power and dosage applied are well below ANSI safety limit for skin exposure (ANSI MPE: 0.02 J/cm$^2$; 0.2 W/cm$^2$ for 300 min).

Lastly, this novel therapeutic platform has photo-selectivity on MRSA and has no photo-toxicity to human cells, as shown in FIG. 33 and its legend.

Materials and Methods
Pump Probe Microscopy

Figure 5:
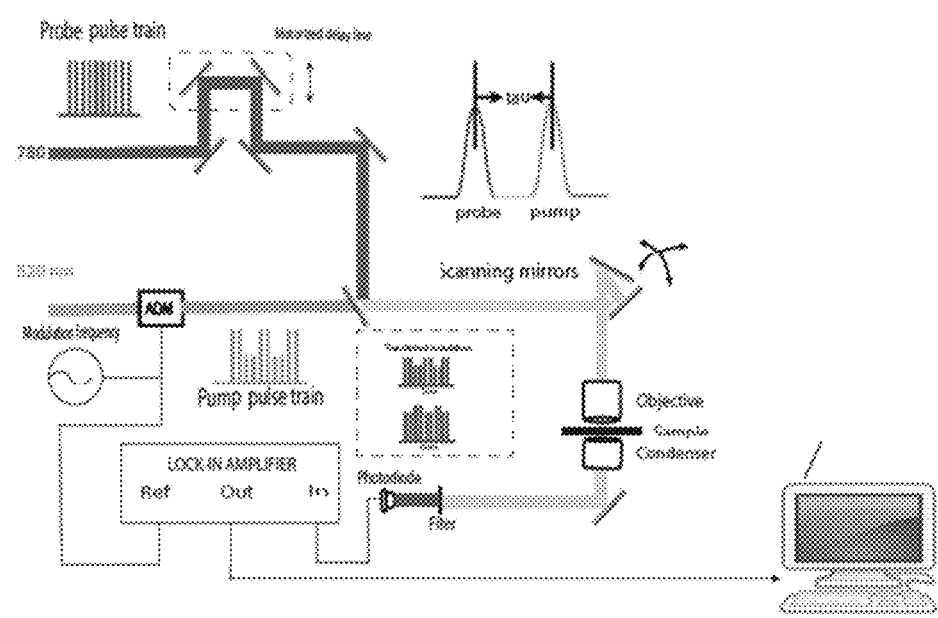
FIG. 5. Schematic illustration of pump probe microscopy.
Figure 9A:
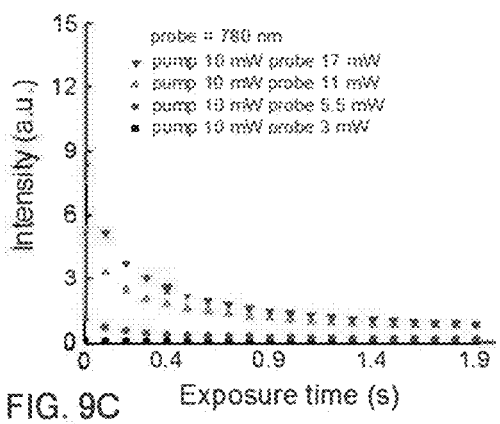
FIG. 9. Characteristics of photobleaching of β-carotene by pump probe microscopy. Time-lapse curves of β-carotene towards probe intensity (FIG. 9A), and pump intensity (FIG. 9B). Normalized time-lapse curves of β-carotene towards probe intensity (FIG. 9C), and pump intensity (FIG. 9D).
Figure 9B:
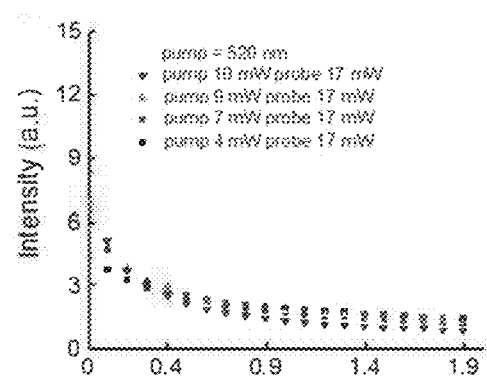
Figure 9C:
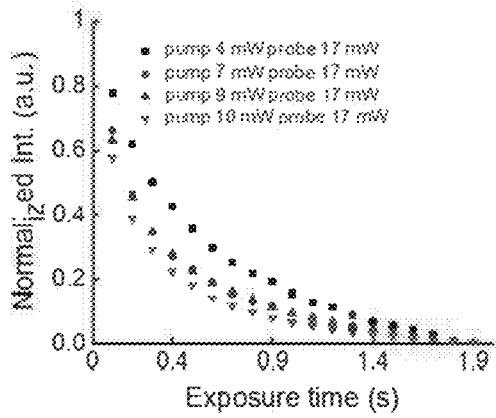
Figure 9D:
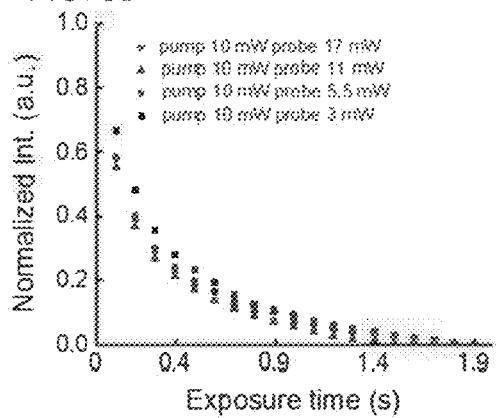

As presented in FIG. 5, an optical parametric oscillator pumped by a high-intensity mode-locked laser generates synchronous pump (520 nm) and probe (probe)pulse trains. The Ti:Sapphire oscillator is split to separate pump and probe pulse trains. Temporal delay between the pump and probe pulses is reached by guiding the pump beam through a computer-controlled delay line. Pump beam intensity is modulated with an acousto-optic modulator (AOM) and the intensity of both beams is adjusted through the combination of a half-wave plate and polarizer. Thereafter, pump and probe beams are collinearly guided into the microscope. After the interaction between the pump beam and the sample, the modulation is transferred to the un-modulated probe beam. Computer-controlled scanning galvo mirrors are used to scan the combined lasers in a raster scanning manner to create microscopic images. The transmitted light is collected by the oil condenser. Subsequently, the pump beam is spectrally filtered by an optical filter (OF) and the transmitted probe intensity is detected by a home-built photodiode (PD). A phase-sensitive lock-in amplifier then demodulates the detected signal. Therefore, pump-induced transmission changes of the sample versus time delay can be measured from the focus plane. This change over time delay shows different decay signatures from different chemicals, thus offering the origin of the chemical contrast. The real-time photobleaching process was captured and fitted by a mathematical model (derivation see supplementary text).

Low-Level Blue Light Apparatus

Figure 2B:
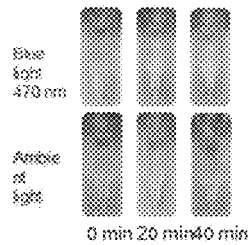
(FIG. 2B). Blue light exposure bleaches *S. aureus* carotenoids.
Figure 2C:
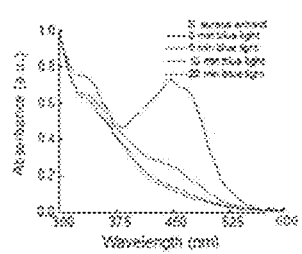
(FIG. 2C). Absorption spectrums of *S. aureus* extract at different blue light exposure time.
Figure 2D:
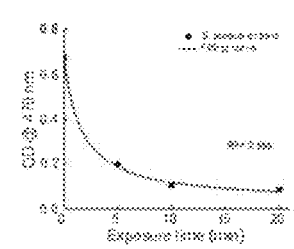
(FIG. 2D). $OD_{470}$ of *S. aureus* extract decreases towards blue light exposure. Curve fitted by equation (1).
Figure 2E:
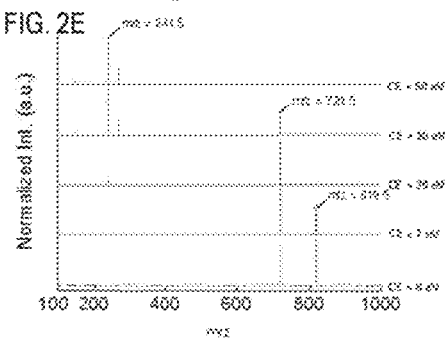
(FIG. 2E). The correlation between m/z=819.5, m/z=721.5 and m/z=241.5 under different collision energies.
Figure 2F:
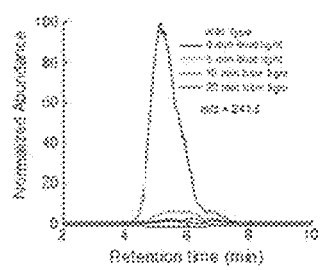
(FIG. 2F). HPLC chromatograph of STX under different blue light exposure time.
Figure 2G:
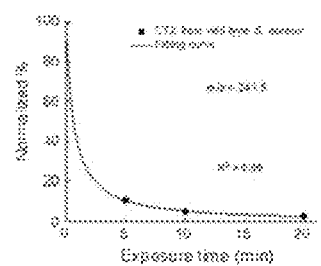
(FIG. 2G). Quantitative analysis of STX attenuation towards blue light exposure. Curve fitted by equation (1).
Figure 2H:
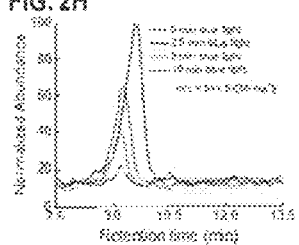
(FIG. 2H-I). TOF-MS/MS analysis of *S. aureus* extract under different blue light exposure time.
Figure 2I:
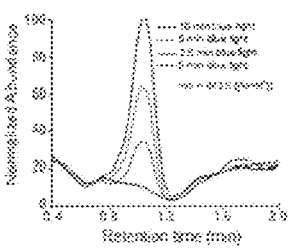
Figure 2J:
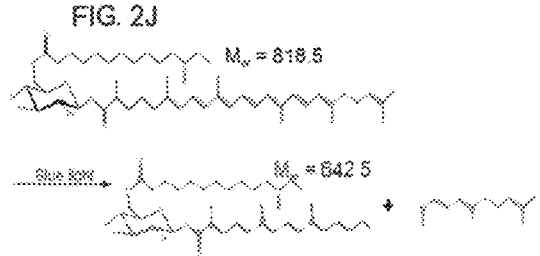
(FIG. 2J). One representative photobleaching process of STX under blue light irradiation.

As depicted in FIG. 2A, the home-built blue light LED has a major wavelength of 460 nm with full width at half maximum of 30 nm. It is comprised of three parts—a blue light LED (M470L3, Thorlabs), an adjustable collimator (COP1-A, Thorlabs), and a power controller (LEDD1B, Thorlabs). The beam spot is adjusted through the adjustable collimator (SM1P25-A, Thorlabs) depending on the size of samples to be treated. The maximal power of the blue light LED is 300 mW.

Absorbance Spectrum of Carotenoid Extract from *S. aureus*

The pigment extraction approach was adapted from a previous report (1). Briefly, 100 μL of bacteria solution supplemented with 1900 μL sterile Luria-Bertani (LB) broth was cultured for 24 hours with shaking (speed of 250 rpm) at 37° C. The suspension was subsequently centrifuged for two minutes at 7,000 rpm, washed once, and re-centrifuged. The pigment was extracted with 200 μL methanol at 55° C. for 20 minutes. Pigments from the CrtM mutant were extracted following the same method described above. For the treatment of *S. aureus* with naftifine, the protocol was adapted from a published report (2). Bacteria were cultured as described above in the presence of, 0.2 mM naftifine. The extraction procedure following the same method described above. The extracted solutions were subsequently exposed to blue light (90 mW, aperture: 1 cm×1 cm) at different time intervals (0 min, 5 min, 10 min, 20 min). Absorption spectra of the above solutions were obtained from a spectrometer (SpectraMax, M5).

Mass Spectrometry for Photobleaching of STX

To study the photobleaching effect on STX, we extracted STX from *S. aureus* and exposed the extract to blue light using the procedure described above. The separation was performed on an Agilent Rapid Res 1200 high performance liquid chromatography (HPLC) system. The HPLC-MS/MS system consisted of a quaternary pump with a vacuum degasser, thermostated column compartment, auto-sampler, data acquisition card (DAD), and triple quadrupole Mass Spectrometer (QQQ) from Agilent Technologies (Palo Alto, Calif., USA). An Agilent (ZORBAX) SB-C8 column (particle size: 3.5 μm, length: 50 mm, and internal diameter: 4.6 mm) was used at a flow rate of 0.8 mL/min. The mobile phase A was water with 0.1% formic acid and mobile phase B was acetonitrile with 0.1% formic acid. The gradient increased linearly as follows: 5% B, from one to five min; 95% B from five to six min, and 5% B. Column re-equilibration was 6-10 min, 5% B. The relative concentration of STX was quantified using MS/MS utilizing the Agilent 6460 Triple Quadrupole mass spectrometer with positive electrospray ionization (ESI). Quantitation was based on multiple reaction monitoring. Mass spectra were acquired simultaneously using electrospray ionization in the positive modes over the range of m/z 100 to 1000. Nitrogen was used as the drying gas flow.

In order to understand how STX degrades when exposed to blue light, an Agilent 6545 Q-TOF (Agilent, Santa Clara, Calif., USA) was exploited to conduct the separation and quantification steps. This ultra-performance liquid chromatography (UPLC)-MS/MS utilized an Agilent (ZORBAX) SB-C8 column (particle size: 3.5 μm, length: 50 mm, and internal diameter: 4.6 mm) to conduct the separation at a flow rate of 0.8 mL/min. The relative concentration of STX was quantified using MS/MS utilizing the Agilent 6545 quadrupole time of flight (Q-TOF) MS/MS with positive ESI. The mobile phase was composed of water (A) and acetonitrile (B). The gradient solution with a flow rate of 0.8 mlUmin was performed as follows: 85% B, from 0 to 30 min; 95% B, from 30 to 31 min; 85% B, from 31 to 35 min; 85% B, after 35 min. The sample injection volume was 20 μL. The UPLC-MS/MS analysis was performed in positive ion modes in the range of m/z 100-1100.

In Vitro Assessment of Synergy Between Blue Light and $H_2O_2$

MRSA USA300 was cultured in sterile LB broth in a 37° C. incubator with shaking (at 250 rpm) until the suspension reached the logarithmic growth phase ($OD_{600}$=0.6). Thereafter, an aliquot (20 μL) of the bacterial suspension was transferred onto a glass slide. Samples were exposed to blue light at different time-lengths and variable light intensities. For groups treated with hydrogen peroxide, bacteria were collected in either LB or phosphate-buffered saline (PBS) supplemented with hydrogen peroxide at different concentrations (0 mM, 0.8 mM, 1.6 mM, 3.3 mM, 6.6 mM, and 13.2 mM). The solutions were cultured for 20 min. The solution was serially diluted in sterile PBS and transferred to LB plates in order to enumerate the viable number of MRSA colony-forming units (CFUs). Plates were incubated at 37° C. for 24 hours before counting viable CFU/mL. Data are presented as viable MRSA CFU/mL and percent survival of MRSA CFU/mL in the treated groups. The data was analyzed via a two-paired t-test (OriginPro 2017). Synergistic effect was confirmed by an equation (see supplementary text).

Fluorescence Mapping of Live/Dead *S. aureus* in Biofilm

An overnight culture of *S. aureus* (ATCC 6538) was grown in a 37° C. incubator with shaking (at 250 rpm). Poly-D-lysine (Sigma Aldrich) was applied to coat the surface of glass bottom dishes (35 mm, In Vitro Scientific) overnight. The overnight culture of *S. aureus* was diluted (1:100) in LB containing 5% glucose and transferred to the glass bottom dishes. The plates were incubated at 37° C. for 24-48 hours in order to form mature biofilm. Thereafter, the media was removed the surface of the dish was washed with sterile water to remove planktonic bacteria. Plates were subsequently treated with blue light alone (200 mW/cm$^2$, 30 min), hydrogen peroxide (13.2 mM, 20 minutes) alone, or a combination of both. Groups receiving $H_2O_2$ were quenched through addition of 0.5 mg/mL catalase (Sigma Aldrich, 50 mM, pH=7 in potassium buffered solution). After treatment, biofilms were immediately stained with fluorescence dyes, as follows.

To confirm the existence of biofilm on the glass bottom surface, a biofilm matrix stain (SYPRO® Ruby Biofilm Matrix Stain, Invitrogen) was utilized. Biofilms were stained with the LIVE/DEAD biofilm viability kit (Invitrogen) for 30 minutes. The biofilms were washed with sterile water twice and then imaged using a fluorescence microscope (OLYMPUS BX51, objective: 60×, oil immersion, NA=1.5). Two different excitation channels (Live: FITC, Dead: Texas Red) were utilized in order to map the ratio of live versus dead cells within the biofilm. The acquired images were analyzed by ImageJ. Statistical analysis was conducted via a two-paired t-test through GraphPad Prism 6.0 (GraphPad Software, La Jolla, Calif.).

Intracellular MRSA Infection Model

Murine macrophage cells (J774) were cultured in Dulbecco's Modified Eagle Medium (DMEM) supplemented with 10% fetal bovine serum (FBS) at 37° C. with $CO_2$ (5%). Cells were exposed to MRSA USA400 at a multiplicity of infection of approximately 100:1. 1-hpost-infection, J774 cells were washed with gentamicin (50 µg/mL, for one hour) to kill extracellular MRSA. Vancomycin, at a concentration equal to 2 µg/mL (4×minimum inhibitory concentration (MIC)), was added to six wells. Six wells received blue light treatment twice (six hours between treatments) for two minutes prior to addition of DMEM+10% FBS. Three wells were left untreated (medium+FBS) and three wells received dimethyl sulfoxide at a volume equal to vancomycin-treated wells. Twelve hours after the second blue light treatment, the test agents were removed; J774 cells were washed with gentamicin (50 µg/mL) and subsequently lysed using 0.1% Triton-X 100. The solution was serially diluted in phosphate-buffered saline and transferred to Tryptic soy agar plates in order to enumerate the MRSA colony-forming units (CFU) present inside infected J774 cells. Plates were incubated at 37° C. for 22 hours before counting viable CFU/mL. Data are presented as $\log_{10}$ (MRSA CFU/mL) in infected J774 cells in relation to the untreated control. The data was analyzed via a two-paired t-test, utilizing GraphPad Prism 6.0 (GraphPad Software, La Jolla, Calif.).

In Vivo MRSA Mice Wound Model

To initiate the formation of a skin wound, five groups (n=5) of eight-week old female Balb/c mice (obtained from Harlan Laboratories, Indianapolis, Ind., USA) were disinfected with ethanol (70%) and shaved on the middle of the back (approximately a one-inch by one-inch square region around the injection site) one day prior to infection as described from a reported procedure (3). To prepare the bacterial inoculum, an aliquot of overnight culture of MRSA USA300 was transferred to fresh Tryptic soy broth and shaken at 37° C. until an $OD_{600}$ value of ~1.0 was achieved. The cells were centrifuged, washed once with PBS, re-centrifuged, and then re-suspended in PBS. Mice subsequently received an intradermal injection (40 µL) containing $2.40 \times 10^9$ CFU/mL MRSA USA300. An open wound formed at the site of injection for each mouse, ~60 hrs post-infection.

Topical treatment was initiated subsequently with each group of mice receiving the following: fusidic acid (2%, using petroleum jelly as the vehicle), 13.2 mM $H_2O_2$ (0.045%, two-minute exposure), blue light (two-minute exposure, 24 J/cm$^2$), or a combination of blue light (two-minute exposure)+13.2 mM $H_2O_2$ (two-minute exposure). One group of mice was left untreated (negative control). Each group of mice receiving a particular treatment regimen was housed separately in a ventilated cage with appropriate bedding, food, and water. Mice were checked twice daily during infection and treatment to ensure no adverse reactions were observed. Mice were treated twice daily (once every 12 hours) for three days, before they were humanely euthanized via $CO_2$ asphyxiation 12 hours after the last dose was administered. The region around the skin wound was lightly swabbed with ethanol (70%) and excised. The tissue was subsequently homogenized in PBS. The homogenized tissue was then serially diluted in PBS before plating onto mannitol salt agar plates. Plates were incubated for at least 19 hours at 37° C. before viable MRSA CFU/mL were counted for each group. Outlier was removed based upon the Dixon Q Test. Data were analyzed via a two-paired t-test, utilizing GraphPad Prism 6.0 (GraphPad Software, La Jolla, Calif.).

Statistical Analysis

Data are means (black) with standard error of mean (red). Statistical analysis was conducted through two-paired t-test. * means significantly different with the p-value<0.001.  means significantly different with the p-value<0.01. * means significantly different with the p-value<0.05.

Supplementary Text

Mathematical Model to Fit the Photobleaching Process Captured by Real-Time Transient Absorption Microscopy Here, we utilized a mathematical model which was originally used to depict the photobleaching of photosensitizers happening during the photodynamic process (4):

$$\frac{d[C]}{dt} = -k_1[C][R], \tag{1}$$

where t is the duration time, [C] is the concentration of chromophore (carotenoids for *S. aureus*), $k_1$ ($k_1=1/\tau_1$) is the rate constant of first-order photobleaching which $\tau_{r1}$ is the first order photobleaching time and [R] is the concentration of active agents (the chromophores which have interaction with light), here:

$$[R] \sim [R]_0 + k_2[C] \tag{2}$$

where $k_2$ ($k_2=1/\tau_2$) is the rate constant of second-order photobleaching which $\tau_2$ is the second order photobleaching time, $[R]_0$ is the original concentration of active agent, respectively. Combined equation (1) and equation (2) together, $$\frac{d[C]}{dt} = -\frac{1}{\tau_1}*[C] - \frac{1}{\tau_2*[C]_0}*[C]^2 \quad (3)$$

the solution for equation (3) is:

$$\frac{[C]_t}{[C]_0} = A * \frac{\exp\left(-\frac{t}{\tau_1}\right)}{1 + \frac{\tau_1}{\tau_2}*\left(1 - \exp\left(-\frac{t}{\tau_1}\right)\right)}, \quad (4)$$

where A is a constant. When first order photobleaching process pivots (usually happening for low concentration of chromophore and the involvement of oxygen), $\tau_2 \to \infty$, equation (4) becomes:

$$\frac{[C]_t}{[C]_0} = A * \exp\left(-\frac{t}{\tau_1}\right), \quad (5)$$

which is similar to first-order kinetic reaction. At this occasion, the photobleaching rate is proportional linearly to the concentration of chromophore. When second order photobleaching process dominates (usually happening for high concentration of chromophore, triplet-triplet annihilation), $\tau_1 \to \infty$, equation (4) becomes:

$$\frac{[C]_t}{[C]_0} = A * \frac{1}{1 + \frac{t}{\tau_2}}, \quad (6)$$

under this condition, the photobleaching rate is proportional to the square of concentration of chromophore. According to the fitting result, S. aureus belongs to second order bleaching with $\tau_1 \to \infty$.

Equation to Determine Synergistic Antimicrobial Effect

The synergistic effect between blue light and $H_2O_2$ was determined by the combination assay as described previously [X]. The fractional inhibitory concentration (FIC) index was calculated as follows: FIC of drug A=MIC of drug A in combination/MIC of drug A alone, FIC of drug B=MIC of drug B in combination/MIC of drug B alone, and FIC index=FIC of drug A+FIC of drug B. An FIC index of ≤0.5 is considered to demonstrate synergy. Additive was defined as an FIC index of 1. Antagonism was defined as an FIC index of >4. According to estimation, in the case of blue light and $H_2O_2$, the FIC is ≤0.38<0.5, thus, blue light exerts synergistic antimicrobial effect with $H_2O_2$ to eradicate MRSA.

REFERENCES

1. D. Diekema et al., 1997-1999. *Clinical Infectious Diseases* 32, S114 (2001).
2. K. Lewis, P. Strandwitz, *Nature* 535, 501 (2016).
3. M. McAdow et al., *PLOS Pathogens* 7, e1002307 (2011).
4. E. Geisinger, R. R. Isberg, *The Journal of Infectious Diseases* 215, S9 (2017).
5. B. Guignard, J. M. Entenza, P. Moreillon, *Current Opinion in Pharmacology* 5, 479 (2005).
6. K. Hiramatsu et al., *Journal of Infection and Chemotherapy* 20, 593 (2014).
7. S. S. Tang, A. Apisarnthanarak, L. Y. Hsu, *Advanced Drug Delivery Reviews* 78, 3 (2014).
8. J. Y. Baek et al., *Journal of Antimicrobial Chemotherapy*, dkx175 (2017).
9. J. R. Smith et al., *Antimicrobial agents and chemotherapy* 60, 3970 (2016).
10. G. Y. Liu et al., *The Journal of experimental medicine* 202, 209 (2005).
11. F. Chen et al., *Nature chemical biology* 12, 174 (2016).
12. C.-I. Liu et al., *Science* 319, 1391 (2008).
13. A. A. Stratonnikov, G. A. Meerovich, V. B. Loschenov, International Society for Optics and Photonics, 2000, pp. 81-91.
14. R. J. Cogdell, H. A. Frank, *Biochimica et Biophysica Acta (BBA)—Reviews on Bioenergetics* 895, 63 (1987).
15. V. Kumar B. N, B. Kampe, P. Rosch, J. Popp, *Analyst* 140, 4584 (2015).
16. N. N. Mishra et al., *Antimicrobial agents and chemotherapy* 55, 526 (2011).
17. W. Min et al., *Nature* 461, 1105 (2009).
18. L. Galassi, *European journal of histochemistry: EJH* 44, 419 (2000).
19. T. Dai et al., *Drug Resistance Updates* 15, 223 (2012).
20. T. Dai et al., *Photomedicine and laser surgery* 31, 531 (2013).
21. S. M. Lehar et al., *Nature* 527, 323 (2015).
22. J. W. Costerton, P. S. Stewart, E. P. Greenberg, *Science* 284, 1318 (1999).
23. S. Ager, K. Gould, *Infection and Drug Resistance* 5, 87 (2012).
24. J. Weigelt et al., *Antimicrobial Agents and Chemotherapy* 49, 2260 (2005).
25. J.-M. Zhang, J. An, *International anesthesiology clinics* 45, 27 (Spring, 2007).

The invention claimed is:

1. A method of sensitizing methicillin-resistant Staphylococcus aureus (MRSA) to antibiotic drugs, consisting essentially of providing a pulsed laser light or a low-level of blue lights below 200 mW per square centimeter to MRSA culture, wherein the pulsed laser light or the low level blue lights create nano-scale pores on functional membrane microdomains of MRSA culture by deleting the yellow pigment of staphyloxanthin (STX) of Staphylococcus aureus.

2. The method according to claim 1, further comprising administering an antibiotic drug selected from the group consisting of cefotaxime, gentamicin, ciprofloxacin, oxacillin, and gentamicin.

3. A method of annihilating of methicillin-resistant *Staphylococcus aureus* (MRSA) in a patient, consisting essentially of providing a pulsed laser light or a low-level of blue lights below 200 mW per square centimeter and administering effective amounts of an oxidative agent to the patient's MRSA infection site.

4. The method according to claim 3, wherein the blue lights and oxidative agent are given at the same time or sequentially.

5. The method according to claim 3, wherein the blue lights are given before the administering of oxidative agent to MRSA culture.

6. The method of claim 3 wherein the patient has an ear infection or an eye infection.

7. The method of claim 3 wherein the patient has skin wound.

8. The method of claim 3 the patient has acne.

9. A treatment regimen for treating methicillin-resistant Staphylococcus aureus (MRSA) infection in a patient, consisting essentially of providing to the patient infection site a laser light or a low-level of blue lights below 200 mW per square centimeter for a period of time, and administering to the patient an effective amount of antibiotics.

10. The treatment regimen according to claim 9, wherein the antibiotics is selected from the group consisting of cefotaxime, gentamicin, ciprofloxacin, oxacillin, and gentamicin.

11. The treatment regimen according to claim 9, wherein the laser light or the low level of blue lights below 200 mW per sequare centimeter is applied to the infection site between about 2 min to about 10 min and has no phototoxicity to the patient.

* * * * *